US012746212B2

(12) United States Patent
Zhang et al.

(10) Patent No.: US 12,746,212 B2
(45) Date of Patent: Sep. 29, 2026

(54) TREATING VASCULATURE RELATED DISEASES OR DISORDERS USING NANOPARTICLES

(71) Applicant: The Regents of the University of California, Oakland, CA (US)

(72) Inventors: Liangfang Zhang, San Diego, CA (US); Che-Ming Jack Hu, Novato, CA (US); Ronnie H. Fang, San Diego, CA (US); Brian T. Luk, San Diego, CA (US); Kuei-Chun Wang, San Diego, CA (US); Shu Chien, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 527 days.

(21) Appl. No.: 17/590,684

(22) Filed: Feb. 1, 2022

(65) Prior Publication Data

US 2022/0151948 A1 May 19, 2022

Related U.S. Application Data

(63) Continuation of application No. 15/737,566, filed as application No. PCT/US2016/036139 on Jun. 7, 2016, now Pat. No. 11,241,394.

(60) Provisional application No. 62/181,799, filed on Jun. 19, 2015.

(51) Int. Cl.

| | |
|---|---|
| ***A61K 9/51*** | (2006.01) |
| ***A61K 31/337*** | (2006.01) |
| ***A61K 47/69*** | (2017.01) |
| ***A61P 7/04*** | (2006.01) |
| ***A61P 9/00*** | (2006.01) |
| ***A61P 35/00*** | (2006.01) |
| ***B82Y 5/00*** | (2011.01) |
| ***B82Y 30/00*** | (2011.01) |

(52) U.S. Cl.
CPC .......... *A61K 9/5176* (2013.01); *A61K 9/5153* (2013.01); *A61K 9/5169* (2013.01); *A61K 31/337* (2013.01); *A61K 47/6901* (2017.08); *A61P 7/04* (2018.01); *A61P 9/00* (2018.01); *A61P 35/00* (2018.01); *B82Y 5/00* (2013.01); *B82Y 30/00* (2013.01)

(58) Field of Classification Search
CPC ........................................................ A61P 35/00
See application file for complete search history.

(56) References Cited

U.S. PATENT DOCUMENTS

| | | | | |
|---|---|---|---|---|
| 5,733,876 | A * | 3/1998 | O'Reilly | G01N 33/68 514/19.3 |
| 2006/0204547 | A1 | 9/2006 | Nguyen | |
| 2008/0248030 | A1 * | 10/2008 | Folkman | A61P 9/00 424/133.1 |
| 2011/0052715 | A1 | 3/2011 | Davis et al. | |
| 2013/0330402 | A1 * | 12/2013 | Smith | A61K 47/42 424/174.1 |
| 2013/0337066 | A1 | 12/2013 | Zhang et al. | |

FOREIGN PATENT DOCUMENTS

| | | |
|---|---|---|
| EP | 0805678 B1 | 10/2003 |

OTHER PUBLICATIONS

Liu et al., "Cancer gene therapy targeting angiogenesis: An updated review", Nov. 21, 2006; 12(43):6941-6948. (Year: 2006).*
PCT International Search Report and Written Opinion for PCT Application No. PCT/US2016/036139 mailed Sep. 7, 2016 (10 pages).
Hu et al., "Anticancer Platelet-Mimicking Nanovehicles," Advanced Materials, 2015, 27:7043-7050.
Weingart et al., "Membrane Mimetic Surface Functionalization of Nanoparticles: Methods and Applications," Advances in Colloid and Interface Science, 2013, 197-198, 68-84.
Xu et al., "Cancer Nanomedicine: From Targeted Delivery to Combination Therapy," Trends Mol Med, 2015, 21 (4):223-232.

* cited by examiner

*Primary Examiner* — Gina C Justice
(74) *Attorney, Agent, or Firm* — Eversheds Sutherland (US) LLP

(57) ABSTRACT

The present invention relates to prevention and/or treatment of diseases or disorders associated with a damaged or leaky vasculature in a subject. The present invention provides for methods, combinations and pharmaceutical compositions for preventing and/or treating a disease or disorder associated with a damaged or leaky vasculature in a subject, using, inter alia, an effective amount of a nanoparticle comprising an inner core comprising a non-cellular material, an outer surface comprising a cellular membrane derived from a platelet; and optionally an agent for preventing, treating, diagnosing, or prognosing the disease or disorder and/or monitoring prevention or treatment of the disease or disorder. Exemplary diseases or disorders include hemorrhage (bleeding), cardiovascular diseases or disorders, diseases or disorders associated with narrowing of a blood vessel, tumors or cancers.

17 Claims, 31 Drawing Sheets

| | Size (nm) | Zeta Potential (mV) | PDI | Drug Loading (wt%) |
|---|---|---|---|---|
| PNP-Docetaxel | 113.4±1.2 | -29.5±1.2 | 0.11 | 2.1±0.04 |
| PNP-Vacomycin | 200.3±3.1 | -30.2±1.0 | 0.24 | 4.0±0.23 |
| RBCNP-Vancomycin | 202.3±2.4 | -29.5±1.7 | 0.22 | 4.1±0.17 |

TREATING VASCULATURE RELATED DISEASES OR DISORDERS USING NANOPARTICLES

CROSS REFERENCE TO RELATED APPLICATIONS

This application is a continuation application of U.S. Ser. No. 15/737,566 filed Dec. 18, 2017, which claims the priority benefit of PCT/US2016/036139 filed on Jun. 7, 2016, which claims the benefit of U.S. Provisional Application No. 62/181,799, filed Jun. 19, 2015 the entire contents of which are hereby incorporated by reference herein.

STATEMENT REGARDING FEDERALLY SPONSORED RESEARCH

This invention was made with government support under Grant No. DK095168 awarded by the National Institutes of Health and under Grant No. HDTRA1-14-1-0064 awarded by the Defense Threat Reduction Agency. The government has certain rights in the invention.

FIELD OF THE INVENTION

The present invention relates to prevention and/or treatment of diseases or disorders associated with a damaged or leaky vasculature in a subject. The present invention provides for methods, combinations and pharmaceutical compositions for preventing and/or treating (and/or related uses) a disease or disorder associated with a damaged or leaky vasculature in a subject, using, inter alia, an effective amount of a nanoparticle comprising an inner core comprising a non-cellular material, an outer surface comprising a cellular membrane derived from a platelet; and optionally an agent for preventing, treating, diagnosing, or prognosing the disease or disorder and/or monitoring prevention or treatment of the disease or disorder. Exemplary diseases or disorders include hemorrhage (bleeding), cardiovascular diseases or disorders, diseases or disorders associated with narrowing of a blood vessel, tumors or cancers.

BACKGROUND OF THE INVENTION

Development of functional nanoparticles can be encumbered by unanticipated material properties and biological events, which can negatively impact nanoparticle effectiveness in complex, physiologically relevant systems[1-3]. Despite the advances in bottom-up nanoengineering and surface chemistry, reductionist functionalization approaches remain inadequate in replicating the complex interfaces present in nature and cannot avoid exposure of foreign materials.

New methods and compositions for preventing and/or treating (and/or related uses) diseases or disorders associated with a damaged or leaky vasculature in a subject are needed. The present disclosure addresses this and the related needs in the art.

SUMMARY OF THE INVENTION

In one aspect, the present invention provides for a method for preventing and/or treating (and/or related uses) a disease or disorder associated with a damaged or leaky vasculature in a subject, which method comprises administering, to a subject in need, or to cells of said subject, an effective amount of a nanoparticle comprising a) an inner core comprising a non-cellular material, b) an outer surface comprising a cellular membrane derived from a platelet; and optionally c) an agent for preventing said disease or disorder, treating said disease or disorder, diagnosing said disease or disorder, prognosing said disease or disorder and/or monitoring prevention or treatment of said disease or disorder.

In another aspect, the present invention is directed to use of an effective amount of a nanoparticle for the manufacture of a medicament for preventing and/or treating (and/or related uses) a disease or disorder associated with a damaged or leaky vasculature in a subject, wherein said nanoparticle comprises: a) an inner core comprising a non-cellular material, b) an outer surface comprising a cellular membrane derived from a platelet; and optionally c) an agent for preventing said disease or disorder, treating said disease or disorder, diagnosing said disease or disorder, prognosing said disease or disorder and/or monitoring prevention or treatment of said disease or disorder.

In still another aspect, the present invention provides for a combination for preventing and/or treating (and/or related uses) a disease or disorder associated with a damaged or leaky vasculature in a subject, which combination comprises an effective amount of a nanoparticle and an effective amount of a second prophylactic or therapeutic agent for preventing and/or treating a disease or disorder associated with a damaged or leaky vasculature in a subject, wherein said nanoparticle comprises: a) an inner core comprising a non-cellular material, h) an outer surface comprising a cellular membrane derived from a platelet; and optionally c) an agent for preventing said disease or disorder, treating said disease or disorder, diagnosing said disease or disorder, prognosing said disease or disorder and/or monitoring prevention or treatment of said disease or disorder.

In some aspects, the prevent disclosure relates to U.S. application Ser. No. 13/827,906, filed Mar. 14, 2013, International Application No. PCT/US2012/039411, filed May 24, 2012 and published as WO 2013/052167 A2 and U.S. provisional application Ser. No. 61/492,626, filed Jun. 2, 2011. The contents of the above applications are incorporated by reference in their entireties.

BRIEF DESCRIPTION OF THE DRAWINGS

FIG. 1A shows physicochemical characterization of platelets, platelet membrane-derived vesicles (platelet vesicles), bare PLGA nanoparticles (bare NPs), and PNPs (n=3). FIG. 1B shows TEM images of bare NPs (left) and PNPs (right) negatively stained with uranyl acetate. Scale bar=100 nm. FIG. 1C shows Dynamic light scattering characterization of particle diameter of bare NPs and PNPs in water and in 1×PBS (n=3). FIG. 1D shows membrane protein translocation onto PNPs resolved using western blotting. FIG. 1E shows TEM image of PNPs negatively stained with vanadium, primary stained with extracellular-domain-specific anti-CD47, and secondary stained by an immunogold conjugate. Scale bar=40 nm. FIGS. 1F-1H show platelet-activating contents including (FIG. 1F) thrombin, (FIG. 1G) ADP, and (FIG. 1H) thromboxane in platelets, platelet vesicles, and PNPs were quantified (n=3). FIG. 1I shows platelet aggregation assay in which citrate-stabilized platelet rich plasma (PRP) was mixed with PBS, PNPs, or thrombin followed by spectroscopic examination of solution turbidity. A decrease in solution turbidity indicates platelet aggregation and sedimentation. All bars represent means±SD.

FIG. 2A shows fluorescence quantification of nanoparticle retention on collagen-coated and non-coated plates (n=6). FIG. 2B shows Localization of PNPs (stained in red) on collagen-coated tissue culture slides seeded with HUVECs (nuclei stained in blue). Cellular periphery is outlined based on cytosolic staining. Scale bar=10 μm. FIG. 2C shows A pseudocolored SEM image of the extracellular matrix of a decellularized human umbilical cord artery following PNP incubation. Particles of approximately 100 nm can be observed on the substrate (colored in orange). Scale bar=500 nm. FIG. 2D shows flow cytometric analysis of nanoparticle uptake by human THP-1 macrophage-like cells (n=3). FIG. 2E shows classical complement activation as measured by C4d split products and FIG. 2F shows alternative complement activation as measured by Bb split products for bare NPs, platelet vesicles, and PNPs in autologous human plasma (n=4). Zymosan and untreated plasma are used as positive and negative controls respectively. All bars represent means±SD. *P≤0.05, P≤0.01, *P≤0.001.

FIG. 3A shows H&E-stained cross-sections of non-damaged (top) and damaged (bottom) human carotid arteries show endothelial denudation following scraping by forceps. Scale bar=200 μm. FIG. 3B shows fluorescence images of undamaged (top) and damaged (bottom) artery cross-sections following PNP incubation (tissue in green and PNPs in red). Scale bar=200 μm. FIG. 3C shows fluorescence visualization of the luminal side of undamaged (top) and damaged (bottom) arteries following PNP incubation (PNPs in red). Scale bar=500 μm. (FIGS. 3D-3E) 3D-reconstructed images of intact (top) and balloon-denuded (bottom) arterial walls from multisectional images following intravenous administration of fluorescently labeled PNPs in rats that received angioplasty-induced arterial denudation (cell nuclei in blue and PNPs in red). Dimensions: 152.5 μm×116 μm×41 μm. FIG. 3F shows retention of fluorescently labeled PNPs at the denuded arteries versus the non-denuded arteries over 120 h following PNP administration (n=6). FIG. 3G shows representative H&E-stained arterial cross-sections from different treatment groups in a rat model of coronary restenosis. Scale bar=200 μm. FIG. 3H shows zoomed-in H&E-stained arterial cross-sections highlight the different vascular remodeling from the different treatment groups. I, intima; M, media. Scale bar=100 μm. FIG. 3I shows quantitative analysis of intima-to-media area ratio from the different treatment groups (n=6). FIG. 3J shows quantitative analysis of luminal obliteration from the different treatment groups (n-=6). All bars represent means±SD. NS=no statistical significance.

FIG. 4A shows a schematic depicting the preparation of PNPs and their resulting functionalities. Poly (lactic-co-glycolic acid) (PLGA) nanoparticles are enclosed entirely in plasma membrane derived from human platelets. The resulting particles possess platelet-mimicking properties for immunocompatibility, subendothelium binding, and pathogen adhesion. FIG. 4B shows a schematic depicting the process of preparing platelet membrane-cloaked nanoparticles (PNPs).

FIG. 5A shows isolation of platelet rich plasma (PRP) was achieved via centrifugation at 100×g. PRP was collected from the top layer (yellow) separated from the red blood cells (red, bottom layer). FIG. 5B shows collected human platelets under light microscopy, which possess a distinctive morphology from FIG. 5C red blood cells. Scale bars=10 μm. FIG. 5D shows transmission electron micrographs of platelet membrane vesicles and FIG. 5E shows PNPs, both of which were negatively stained with 1% uranyl acetate. Scale bars=200 nm. FIG. 5F shows dynamic light scattering measurements of PNPs in 10% sucrose show that the particles retain their size and stability following a freeze-thaw cycle and resuspension upon lyophilization (n=3). Bars represent means±SD. FIG. 5G shows transmission electron micrograph shows retentions of PNPs' core-shell structure following a freeze-thaw cycle in 10% sucrose. Scale bar=100 nm. FIG. 5J shows transmission electron micrograph shows retentions of PNPs' core-shell structure upon resuspension following lyophilization in 10% sucrose. Scale bar=100 nm.

FIG. 7A shows transmission electron micrograph of PNPs primary stained with anti-CD47 (intracellular), secondary stained with immunogold, and negatively stained with 2% vanadium. The immunogold staining revealed presence of intracellular CD47 domains on collapsed platelet membrane vesicles but not on PNPs. FIG. 7A shows transmission electron micrograph of PNPs primary stained with anti-CD47 (extracellular), secondary stained with immunogold, and negatively stained with 2% vanadium. PNPs are shown to display extracellular CD47 domains. All scale bars=100 nm. FIG. 7C shows 2 μm polystyrene beads were functionalized with anti-CD47 against the protein's extracellular domain, anti-CD47 against the protein's intracellular domain, or a sham antibody. Flow cytometric analysis of the different beads following DiD-loaded PNP incubation shows the highest particle retention to beads functionalized with anti-CD47 against the protein's extracellular domain. FIG. 7D shows normalized fluorescence intensity of PNP retention to the different antibody-functionalized beads. Bars represent means±SEM.

FIGS. 8A-8C show representative fluorescence images visualizing DiD-loaded PNPs (red grey scales), cellular cytosol (green grey scales), and cellular nuclei (blue grey scales). FIGS. 8D-8F show images showing only the red and blue channels in order to highlight the differential localization of PNPs. Scale bar=10 μm.

FIG. 9A shows DiD-loaded PNPs were injected intravenously through the tail vein of Sprague-Dawley rats. At various time points blood was withdrawn via tail vein blood sampling for fluorescence quantification to evaluate the systemic circulation lifetime of the nanoparticles (n=6). FIG. 9B shows biodistribution of the PNP nanoparticles in balloon-denuded Sprague-Dawley rats at 2 h and 48 h following intravenous nanoparticle administration through the tail vein (n=6). FIG. 9C shows comprehensive metabolic panel of rats following injections with human-derived PNPs and PBS (n=6). The rats received intravenous injections of PNPs and PBS on day 0 and day 5, and the blood test conducted on day 10 did not reveal significant changes between the two groups, indicating normal liver and kidney functions following the PNP administration. All bars and markers represent means±SD.

FIG. 10A shows fluorescence microscopy of the aortic branch revealed selective PNP binding to the denuded artery (right) as opposed to the undamaged artery (left) (PNP fluorescence in red grey scales). FIG. 10B shows Fluorescence images acquired from the control artery, which did not reveal PNP fluorescence upon focusing on either the endothelium (top) or the smooth muscle layer (bottom) (nuclei in blue red scales). FIG. 10C shows fluorescence images acquired from the denuded artery, which revealed significant PNP retention as fluorescent punctuates (PNP fluorescence in red grey scales) above the smooth muscle layer. FIG. 10D shows fluorescence image of arterial cross-section acquired from the control artery, which showed nuclei of endothelial cells above the collagen layer (autofluorescence in green grey scales) and an absence of PNP fluorescence. FIG. 10E shows fluorescence image of arterial cross-section acquired from the denuded artery, which showed PNP retention as fluorescent punctuates on the collagen layer (PNP fluorescence in red; collagen autofluorescence in green grey scales) and an absence of endothelial cell nuclei. All scale bars=100 μm.

FIG. 11A shows physicochemical properties of drug-loaded cell membrane cloaked nanoparticles. FIG. 11B shows TEM visualization of docetaxel-loaded PNPs (PNP-Dtxl). Scale bar=200 nm. FIG. 11C shows a drug release profile of PNP-Dtxl as compared to PEG-PLGA diblock nanoparticles of equivalent size and docetaxel loading (n=3). FIG. 11D shows TEM visualization of vancomycin-loaded PNPs (PNP-Vanc). Scale bar=200 nm. FIG. 11E shows drug release profiles of PNP-Vanc and RBCNP-Vanc (n=3). Bars represent means±SD.

DETAILED DESCRIPTION OF THE INVENTION

Figure 1A:
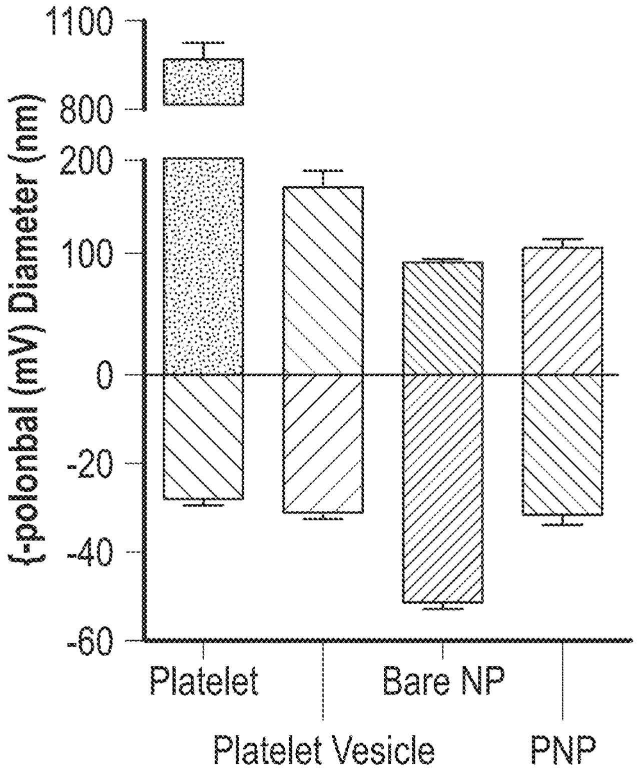
FIGS. 1A-1I show preparation and characterization of PNPs.
Figure 1B:
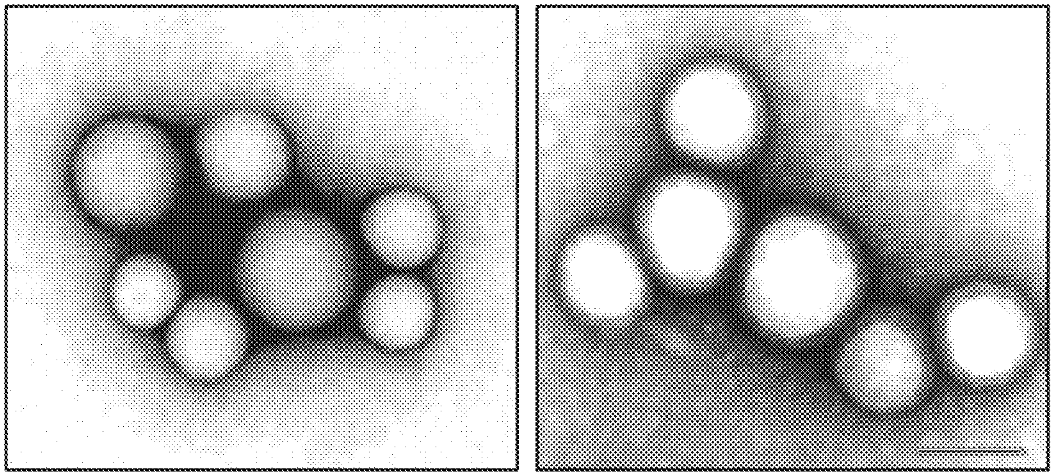

The practice of the present invention will employ, unless otherwise indicated, conventional techniques of nanotechnology, nano-engineering, molecular biology (including recombinant techniques), microbiology, cell biology, biochemistry, immunology, and pharmacology, which are within the skill of the art. Such techniques are explained fully in the literature, such as, *Molecular Cloning: A Laboratory Manual,* 2nd ed. (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds., 1987, and periodic updates); *PCR: The Polymerase Chain Reaction* (Mullis et al., eds., 1994); and Remington, *The Science and Practice of Pharmacy,* 20th ed., (Lippincott, Williams & Wilkins 2003).

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. Definitions

To facilitate understanding of the invention, a number of terms and abbreviations as used herein are defined below as follows:

When introducing elements of the present invention or the preferred embodiment(s) thereof, the articles “a”, “an”, “the” and “said” are intended to mean that there are one or more of the elements. The terms “comprising”, “including” and “having” are intended to be inclusive and mean that there may be additional elements other than the listed elements.

The term “and/or” when used in a list of two or more items, means that any one of the listed items can be employed by itself or in combination with any one or more of the listed items. For example, the expression “A and/or B” is intended to mean either or both of A and B, i.e. A alone, B alone or A and B in combination. The expression “A, B and/or C” is intended to mean A alone, B alone, C alone, A and B in combination, A and C in combination, B and C in combination or A, B. and C in combination.

Cellular Membrane: The term “cellular membrane” as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom. As used herein, the term “naturally occurring” refers to one existing in nature. As used herein, the term “derived therefrom” refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell or a virus and the prepared or isolated membrane can be combined with other substances or materials to form a derived membrane. In another example, a cell or virus can be recombinantly engineered to produce “non-natural” substances that are incorporated into its membrane in vivo, and the cellular or viral membrane can be prepared or isolated from the cell or the virus to form a derived membrane.

In various embodiments, the cellular membrane covering either of the unilamellar or multilamellar nanoparticles can be further modified to be saturated or unsaturated with other lipid components, such as cholesterol, free fatty acids, and phospholipids, and also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle. In other examples, functional groups such as antibodies and aptamers can be added to the outer surface of the membrane to enhance site targeting, such as to cell surface epitopes found in cancer cells. The membrane of the nanoparticles can also comprise particles that can be biodegradable, cationic nanoparticles including, but not limited to, gold, silver, and synthetic nanoparticles.

Synthetic or artificial membrane: As used herein, the term "synthetic membrane" or "artificial membrane" refers to a man-made membrane that is produced from organic material, such as polymers and liquids, as well as inorganic materials. A wide variety of synthetic membranes are well known in the art.

Nanoparticle: The term "nanoparticle" as used herein refers to nanostructure, particles, vesicles, or fragments thereof having at least one dimension (e.g., height, length, width, or diameter) of between about 1 nm and about 10 μm. For systemic use, an average diameter of about 50 nm to about 500 nm, or 100 nm to 250 nm may be preferred. The term "nanostructure" includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. In some embodiments, the nanoparticle comprises or consists of an inner core covered by an outer surface comprising the membrane as discussed herein. The invention contemplates any nanoparticles now known and later developed that can be coated with the membrane described herein.

Pharmaceutically active: The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (PAI) is the pharmaceutically active substance in a drug.

Pharmaceutically acceptable: The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent nanoparticle or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use. Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of a nanoparticle or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A nanoparticle or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrohenzoates, hydroxybenzoates, methoxyhenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

Pharmaceutically acceptable carrier: The term "pharmaceutically acceptable carrier" as used herein refers to an excipient, diluent, preservative, solubilizer, emulsifier, adjuvant, and/or vehicle with which a nanoparticle or compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20'" ed., (Lippincott, Williams & Wilkins 2003). Except insofar as any conventional media or agent is incompatible with the active compound, such use in the compositions is contemplated.

Phospholipid: The term "phospholipid" as used herein, refers to any of numerous lipids containing a diglyceride, a phosphate group, and a simple organic molecule such as choline. Examples of phospholipids include, but are not limited to, Phosphatide acid (phosphatidate) (PA). Phosphatidylethanolamine (cephalin) (PE), Phosphatidylcholine (lecithin) (PC), Phosphatidylserine (PS), and Phosphoinositides which include, but are not limited to, Phosphatidylinositol (PI), Phosphatidylinositol phosphate (PIP). Phosphatidylinositol bisphosphate (PIP2) and Phosphatidylinositol triphosphate (P1P3). Additional examples of PC include DDPC, DLPC, DMPC, DPPC, DSPC, DOPC, POPC, DRPC, and DEPC as defined in the art.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as a hemolytic disease or condition, or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

The term "combination" refers to either a fixed combination in one dosage unit form, or a kit of parts for the combined administration where a nanoparticle or compound and a combination partner (e.g., another drug as explained below, also referred to as "therapeutic agent" or "co-agent") may be administered independently at the same time or separately within time intervals, especially where these time intervals allow the combination partners to show a cooperative, e.g., synergistic, effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a nanoparticle or compound and a combination partner, are both administered to a patient simultaneously in the form of a single entity or dosage. The term "non-fixed combination" means that the active ingredients, e.g., a nanoparticle or compound and a combination partner, are both administered to a patient as separate entities either simultaneously, concurrently or sequentially with no specific time limits, wherein such administration provides therapeutically effective levels of the two moieties or compounds in the body of the patient. The latter also applies to cocktail therapy, e.g., the administration of three or more active ingredients.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

B. Methods for Preventing and/or Treating a Disease or Disorder in a Subject

In one aspect, the present invention provides for a method for preventing and/or treating (and/or related uses) a disease or disorder associated with a damaged or leaky vasculature in a subject, which method comprises administering, to a subject in need, or to cells of said subject, an effective amount of a nanoparticle comprising a) an inner core comprising a non-cellular material, b) an outer surface comprising a cellular membrane derived from a platelet; and optionally c) an agent for preventing said disease or disorder, treating said disease or disorder, diagnosing said disease or disorder, prognosing said disease or disorder and/or monitoring prevention or treatment of said disease or disorder. In some embodiments, the disease or disorder is not a disease or disorder disclosed in U.S. application Ser. No. 13/827,906, filed Mar. 14, 2013, International Application No. PCT/US2012/039411, filed May 24, 2012 and published as WO 2013/052167 A2 and U.S. provisional application Ser. No. 61/492,626, filed Jun. 2, 2011.

The present methods can be used to prevent and/or treat a disease or disorder associated with a damaged or leaky vasculature in any suitable subject. In some embodiments, the subject is a mammal. In some embodiments, the mammal is a human. In other embodiments, the mammal is a non-human mammal, including a pet, a farm animal, an economic animal, a sport animal and an experimental animal, such as a cat, a dog, a horse, a cow, an ox, a pig, a donkey, a sheep, a lamb, a goat, a mouse, a rabbit, a primate, including a monkey and a chimpanzee.

In some embodiments, the present methods can be used for preventing a disease or disorder associated with a damaged or leaky vasculature in a subject. In other embodiments, the present methods can be used for treating a disease or disorder associated with a damaged or leaky vasculature in a subject. The present methods can be used to prevent and/or treat a disease or disorder associated with a damaged or leaky vasculature in a subject to any suitable degree. For example, present methods can be used to decrease or neutralize the effect of a disease or disorder associated with a damaged or leaky vasculature in a subject by at least 10%, 20%, 30%, 40%, 50%, 60%, 70%, 80%, 90%, 91%, 92%, 93%, 94%, 95%, 96%, 97%, 98%, 99% or more compared to a comparable untreated subject or to the same subject at an untreated stage.

The nanoparticle used in the present methods can comprise any suitable inner core. For example, the inner core of the nanoparticle can comprise a polymeric particle core, a silica particle core, or a metal, e.g., gold, particle core. Any suitable polymeric particle core can be used. In some embodiments, the polymeric particle core can comprise an optical shift property. In other embodiments, the polymeric particle core can comprise a metal, e.g., gold, iron oxide or a quantum dot. In still other embodiments, the inner core of the nanoparticle can comprise a biocompatible or a synthetic material, such as poly(lactic-c-glycolic acid) (PLGA), polylactic acid (PLA), polyglycolic acid (PGA), polycaprolactone (PCL), polylysine, and polyglutamic acid. In yet other embodiments, the inner core of the nanoparticle supports the outer surface.

The nanoparticle used in the present methods can comprise any suitable cellular membrane derived from a platelet. For example, the nanoparticle used in the present methods can comprise a plasma membrane derived from a platelet. In another example, the nanoparticle used in the present methods can comprise an intracellular membrane derived from a platelet.

The therapeutic agent, the prophylactic agent, the diagnostic or marker agent, the prognostic agent, the isolation agent, the monitoring agent, or a combination thereof, can be comprised in any suitable location in the composition used in the present methods. For example, the therapeutic agent, the prophylactic agent, the diagnostic or marker agent, the prognostic agent, the isolation agent, the monitoring agent, or a combination thereof, can be comprised in the nanoparticle. In some embodiments, the therapeutic agent, the prophylactic agent, the diagnostic or marker agent, the prognostic agent, the isolation agent, the monitoring agent, or a combination thereof, can be comprised in a releasable cargo in the nanoparticle.

The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or cells of the subject, or by a change of a physical parameter surrounding the nanoparticle. The nanoparticle can comprise any suitable type of a releasable cargo. For example, the releasable cargo can be a metallic particle, a polymeric particle, a dendrimer particle, or an inorganic particle.

In some embodiments, the therapeutic agent, the prophylactic agent, the diagnostic or marker agent, the prognostic agent, the isolation agent, the monitoring agent, or a combination thereof, can be comprised in the composition used in the present methods but outside the nanoparticle. In other embodiments, the therapeutic agent, the prophylactic agent, the diagnostic or marker agent, the prognostic agent, the isolation agent, the monitoring agent, or a combination thereof, can be administered to the subject separately from the composition used in the present methods. The composition used in the present methods and the additional substance can be administered to the subject simultaneously or sequentially.

In some embodiments, the therapeutic agent is used for treating a disease or disorder associated with a damaged or leaky vasculature in a subject. In other embodiments, the prophylactic agent is used for preventing a disease or disorder associated with a damaged or leaky vasculature in a subject. In still other embodiments, the diagnostic or marker agent is used for diagnosing a disease or disorder associated with a damaged or leaky vasculature in a subject. In yet other embodiments, the prognosing or marker agent is used for prognostic a disease or disorder associated with a damaged or leaky vasculature in a subject. In yet other embodiments, the monitoring agent is used for monitoring prevention or treatment of a disease or disorder associated with a damaged or leaky vasculature in a subject. In yet other embodiments, the isolation agent is used for facilitating isolation and removal of a cell, tissue or organ associated with the damaged or leaky vasculature from the subject. The isolation agent can comprise any suitable material. In some embodiments, the isolation agent comprises a magnetic material, e.g., iron oxide.

The nanoparticle used in the present methods can have any suitable size. For example, the nanoparticle can have a diameter from about 10 nm to about 10 μm. In certain embodiments, the diameter of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm, or any sub-range within about 10 nm to about 10 μm, e.g., any range between any two of the above sizes.

The nanoparticle used in the present methods can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle used in the present methods substantially lacks constituents of the platelet from which the cellular membrane is derived. For example, the nanoparticle can lack 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the platelet from which the cellular membrane is derived.

In some embodiments, the nanoparticle used in the present methods substantially maintains the natural structural integrity or activity of the cellular membrane derived from the platelet or the constituents of the cellular membrane derived from the platelet. For example, the nanoparticle can retain 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity or activity for targeting a damaged or leaky vasculature in a subject.

In some embodiments, the nanoparticle used in the present methods is biocompatible or biodegradable. For example, the inner core of the nanoparticle comprises PLGA and the outer surface of the nanoparticle comprises a plasma membrane derived from the platelet.

The nanoparticle used in the present methods can have any suitable half-life in vivo. For example, the nanoparticle can have a half-life in blood circulation in vivo for at least from about 30 minutes to about 10 hours, e.g., about 1, 2, 3, 4, 5, 6, 7, 8, 9, 10 hours.

The outer surface of the nanoparticle used in the present methods can further comprise a synthetic membrane. In some embodiments, the nanoparticles used in the present methods comprise a mixture of nanoparticles that comprise an outer surface comprising a platelet cellular membrane and nanoparticles that comprise an outer surface comprising a synthetic membrane. The nanoparticles that comprise an outer surface comprising a synthetic membrane may or may not be capable of targeting a damaged or leaky vasculature in a subject. In some embodiments, both the nanoparticles that comprise an outer surface comprising a platelet cellular membrane and nanoparticles that comprise an outer surface comprising a synthetic membrane are capable of targeting a damaged or leaky vasculature in a subject. In other embodiments, the nanoparticles that comprise an outer surface comprising a platelet cellular membrane is capable of targeting a damaged or leaky vasculature in a subject, but the nanoparticles that comprise an outer surface comprising a synthetic membrane is not capable of targeting a damaged or leaky vasculature in a subject.

The composition used in the present methods can comprise the nanoparticles that comprise an outer surface comprising a platelet cellular membrane and nanoparticles that comprise an outer surface comprising a synthetic membrane in any suitable ratio. In some embodiments, the present composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a platelet cellular membrane. In other embodiments, the present composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50%, (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a synthetic membrane. For example, the composition used in the present methods can comprise about 1-10% (w/w) of the nanoparticles that comprise an outer surface comprising a platelet cellular membrane and about 90-99% (w/w) of the nanoparticles that comprise an outer surface comprising a synthetic membrane, about 11-25% (w/w) of the nanoparticles that comprise an outer surface comprising a platelet cellular membrane and about 75-89% (w/w) of the nanoparticles that comprise an outer surface comprising a synthetic membrane, about 50% (w/w) of the nanoparticles that comprise an outer surface comprising a platelet cellular membrane and about 50% (w/w) of the nanoparticles that comprise an outer surface comprising a synthetic membrane, about 51-75% (w/w) of the nanoparticles that comprise an outer surface comprising a platelet cellular membrane and about 49-25% (w/w) of the nanoparticles that comprise an outer surface comprising a synthetic membrane, or about 90-100% (w/w) of the nanoparticles that comprise an outer surface comprising a platelet cellular membrane and about 0-10% (w/w) of the nanoparticles that comprise an outer surface comprising a synthetic membrane.

The outer surface of the nanoparticle can comprise a hybrid membrane comprising a cellular membrane derived from a platelet and a synthetic membrane. In some embodiments, the outer surface of the nanoparticle can comprise a hybrid membrane comprising at least about 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w) of a cellular membrane derived from a platelet. In other embodiments, the outer surface of the nanoparticle can comprise a hybrid membrane comprising at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w) of a synthetic membrane. For example, the outer surface of the nanoparticle can comprise a hybrid membrane comprising about 5-10% (w/w) of a cellular membrane derived from a platelet and about 90-95% (w/w) of a synthetic membrane, about 11-25% (w/w) of a cellular membrane derived from a platelet and about 75-89% (w/w) of a synthetic membrane, about 50% (w/w) of a cellular membrane derived from a platelet and about 50% (w/w) of a synthetic membrane, about 51-75% (w/w) of a cellular membrane derived from a platelet and about 49-25% (w/w) of a synthetic membrane, or about 90-99% (w/w) of a cellular membrane derived from a platelet and about 1-10% (w/w) of a synthetic membrane.

In some embodiments, the nanoparticle used in the present methods substantially lacks immunogenicity to the subject, e.g., a mammal. For example, the cellular membrane can be derived from a platelet from the same species of the subject. In another example, the subject is a human and the cellular membrane is derived from a human platelet. In some embodiments, the cellular membrane can be derived from a platelet of the mammal to be treated. For example, the cellular membrane can be derived from a platelet of the human to be treated.

The present methods can be used for preventing and/or treating any suitable disease or disorder associated with a damaged or leaky vasculature in a subject. For example, the present methods can be used for preventing and/or treating a disease or disorder associated with a damaged vasculature in a subject. In another example, the present methods can be used for preventing and/or treating a disease or disorder associated with a leaky vasculature in a subject. In still another example, the present methods can be used for preventing and/or treating hemorrhage (bleeding), a cardiovascular disease or disorder, a disease or disorder associated with narrowing of a blood vessel, a tumor or a cancer that is associated with a damaged or leaky vasculature in a subject.

In some embodiments, the present methods can be used for preventing and/or treating hemorrhage associated with a damaged or leaky vasculature in a subject. The nanoparticle used in the present methods can comprise an agent for preventing the hemorrhage, treating the hemorrhage, diagnosing the hemorrhage, prognosing hemorrhage and/or monitoring prevention or treatment of the hemorrhage.

The present methods can be used for preventing and/or treating any suitable hemorrhage associated with a damaged or leaky vasculature in a subject. In some embodiments, the hemorrhage to be prevented and/or treated is internal hemorrhage or external hemorrhage. In other embodiments, the hemorrhage to be prevented and/or treated is class I hemorrhage, class II hemorrhage, class III hemorrhage or class IV hemorrhage. In still other embodiments, the hemorrhage to be prevented and/or treated is mouth hemorrhage, e.g., hematemesis or hemoptysis, anus hemorrhage, e.g., haematochezia, urinary tract hemorrhage, e.g., hematuria, upper head hemorrhage, e.g., intracranial hemorrhage, cerebral hemorrhage, cerebral hemorrhage, or subarachnoid hemorrhage, lungs hemorrhage, e.g., pulmonary hemorrhage, gynecologic hemorrhage, e.g., vaginal bleeding (such as postpartum bleeding or breakthrough bleeding), or ovarian bleeding, gastrointestinal hemorrhage, e.g., upper gastrointestinal bleeding, lower gastrointestinal bleeding, or occult gastrointestinal bleeding. In yet other embodiments, the hemorrhage to be prevented and/or treated is caused by a traumatic injury, e.g., an abrasion, an excoriation, a hematoma, a laceration, an incision, a puncture wound, a contusion, a crushing injury or a ballistic trauma. In yet other embodiments, the hemorrhage to be prevented and/or treated is caused by a medical condition. For example, the hemorrhage to be prevented and/or treated can be caused by an intravascular change, e.g., increase or decrease of blood pressure or decrease of the level of a clotting factor, an intramural change, e.g., aneurysm, aortic dissection, arteriovenous malformation or vasculitis, or an extravascular change, e.g., *H. pylori* infection, brain abscess or a brain tumor.

In some embodiments, the hemorrhage to be prevented and/or treated is caused by a medication. For example, the hemorrhage to be prevented and/or treated can be caused by a nonsteroidal anti-inflammatory drug, e.g., aspirin or ibuprofen. The nanoparticle used in the present methods can comprise an agent for antagonizing the effect of the nonsteroidal anti-inflammatory drug.

In some embodiments, the hemorrhage to be prevented and/or treated is caused by a deficiency in blood coagulation. For example, the hemorrhage to be prevented and/or treated is haemophilia A caused by deficiency of Factor VIII. The nanoparticle used in the present methods can comprise an effective amount of Factor VIII. In another example, the hemorrhage to be prevented and/or treated is haemophilia B caused by deficiency of Factor IX. The nanoparticle used in the present methods can comprise an effective amount of Factor IX. In still another example, the hemorrhage to be prevented and/or treated is caused by an antibody to Factor VIII. The nanoparticle used in the present methods can comprise an effective amount of an agent for antagonizing the effect of the antibody to Factor VIII. In yet another example, the hemorrhage to be prevented and/or treated is Von Willebrand disease caused by deficiency of the "von Willebrand" factor. The nanoparticle used in the present methods can comprise an effective amount of "von Willebrand" factor. In yet another example, the hemorrhage to be prevented and/or treated is caused by deficiency of Factor VII or Factor XIII. The nanoparticle used in the present methods can comprise an effective amount of Factor VII or Factor XIII. In yet another example, the hemorrhage to be prevented and/or treated is warfarin-related bleeding caused by administration of an antibiotic. The nanoparticle used in the present methods can comprise an effective amount of an agent for antagonizing the effect of the warfarin or the antibiotic, or an effective amount of vitamin K.

In some embodiments, the hemorrhage to be prevented and/or treated occurs during or after a surgery. In some embodiments, the hemorrhage to be prevented and/or treated occurs during or after a warfare, a terror attack, a suicide attempt or an accident.

In some embodiments, the present methods can be used for preventing and/or treating a cardiovascular disease or disorder associated with a damaged or leaky vasculature in a subject. The nanoparticle used in the present methods can comprise an agent for preventing the cardiovascular disease or disorder, treating the cardiovascular disease or disorder, diagnosing the cardiovascular disease or disorder, prognosing the cardiovascular disease or disorder and/or monitoring prevention or treatment of the cardiovascular disease or disorder.

The present methods can be used for preventing and/or treating any suitable cardiovascular disease or disorder associated with a damaged or leaky vasculature in a subject. In some embodiments, the cardiovascular disease or disorder to be prevented and/or treated is a coronary artery disease (CAD) (also known as ischemic heart disease (IHD), atherosclerotic heart disease, atherosclerotic cardiovascular disease or coronary heart disease), a stroke (also known as cerebrovascular accident (CVA), cerebrovascular insult (CVI), or brain attack), a hypertensive heart disease, a rheumatic heart disease (RHD), an atrial fibrillation (AF or A-fib), an aortic aneurysm, a cardiomyopathy, a congenital heart defect (CHD), an endocarditis, or a peripheral artery disease (PAD). In other embodiments, the cardiovascular disease or disorder to be prevented and/or treated is associated with atherosclerosis (also known as arteriosclerotic vascular disease or ASVD).

The nanoparticle used in the present methods can comprise an effective amount of a medication for preventing and/or treating the cardiovascular disease or disorder. Any suitable medication can be used. For example, the medication for preventing and/or treating the cardiovascular disease or disorder can be an ACE inhibitor, an angiotensin II receptor blocker, an antiarrythmic, an antiplatelet medication, aspirin, a beta-blocker, a clot buster (thrombolytic), Coumadin, digoxin, a statin, a diuretic and a vasodilator.

In some embodiments, the present methods can be used for preventing and/or treating a disease or disorder associated with narrowing of a blood vessel in a subject. The nanoparticle used in the present methods can comprise an agent for preventing the disease or disorder associated with narrowing of a blood vessel, treating the disease or disorder associated with narrowing of a blood vessel, diagnosing the disease or disorder associated with narrowing of a blood vessel, prognosing disease or disorder associated with narrowing of a blood vessel and/or monitoring prevention or treatment of the disease or disorder associated with narrowing of a blood vessel.

The present methods can be used for preventing and/or treating any suitable disease or disorder associated with narrowing of a blood vessel in a subject. In some embodiments, the disease or disorder associated with narrowing of a blood vessel to be prevented and/or treated is restenosis. The present methods can be used for preventing and/or treating any suitable restenosis. For example, the restenosis to be prevented and/or treated is restenosis of an artery or restenosis of a blood vessel within an organ. In another example, the restenosis to be prevented and/or treated is an adverse event of an endovascular procedure, e.g., a vascular surgery, a cardiovascular (heart) surgery or an angioplasty (or balloon angioplasty).

The nanoparticle used in the present methods can comprise an effective amount of an agent for inhibiting or reducing tissue growth that contributes to the restenosis. Any suitable agent for inhibiting or reducing tissue growth that contributes to the restenosis can be used. In some embodiments, an agent that inhibits or reduces neointimal hyperplasia can be used. Exemplary agent for inhibiting or reducing neointimal hyperplasia can be an agent for anti-inflammatory treatment, e.g., IL-10, an agent for nitric oxide-based treatment, a glucagon-like peptide-1 receptor (GLP-1) agonist, e.g., exendin-4, or a mitotic inhibitor. Exemplary mitotic inhibitor can be a taxane, e.g., paclitaxel or docetaxel, a vinca alkaloid, e.g., vinblastine, vincristine, vindesine or vinorelbine, colchicine, podophyllotoxin, podophyllin, or griseofulvin. In other embodiments, the restenosis to be prevented and/or treated is coronary restenosis and the nanoparticle comprises an effective amount of docetaxel.

In some embodiments, the nanoparticle used in the present methods can comprise an effective amount of an agent for pro-angiogenic therapy. The agent can be used for gene-therapy or protein-therapy. Any suitable pro-angiogenic agent can be used. For example, the pro-angiogenic agent can be fibroblast growth factor 1 (FGF-1) or a polynucleotide sequence that encodes FGF-1.

In some embodiments, the present methods can be used for preventing and/or treating tumor or a cancer associated with a damaged or leaky vasculature in a subject. The nanoparticle used in the present methods can comprise an agent for preventing the tumor or cancer, treating the tumor or cancer, diagnosing the tumor or cancer, prognosing the tumor or cancer and/or monitoring prevention or treatment of the tumor or cancer.

The present methods can be used for preventing and/or treating any suitable tumor or cancer associated with a damaged or leaky vasculature in a subject. In some embodiments, the tumor or cancer associated with a damaged or leaky vasculature to be prevented and/or treated can be sarcoma, epidermoid cancer, fibrosarcoma, cervical cancer, gastric carcinoma, skin cancer, leukemia, lymphoma, lung cancer, non-small cell lung cancer, colon cancer, CNS cancer, melanoma, ovarian cancer, renal cancer, prostate cancer, breast cancer, liver cancer, head and neck cancers, or pancreatic cancer.

In some embodiments, the tumor or cancer associated with a damaged or leaky vasculature to be prevented and/or treated is associated with tumor angiogenesis. The nanoparticle used in the present methods can comprise an effective amount of an angiogenesis inhibitor. Any suitable angiogenesis inhibitor can be used. Exemplary angiogenesis inhibitor can be angiostatin, endostatin, tumstatin or an antibody against an angiogenesis stimulator, e.g., vascular endothelial growth factor (VEGF). The angiogenesis inhibitor can be used for gene-therapy or protein-therapy.

The present methods can further comprise administering another active ingredient to the subject. The other active ingredient can be used for preventing and/or treating a disease or disorder associated with a damaged or leaky vasculature in a subject.

In some embodiments, the present methods can further comprise administering a pharmaceutically acceptable carrier or excipient to the subject.

The composition used in the present methods can be administered using any suitable delivery mechanisms or techniques. In some embodiments, the composition can be administered alone. In other embodiments, the composition can be administered with a pharmaceutically acceptable carrier or excipient. In still other embodiments, the composition can be administered via a medicament delivery system or a medical device. Any suitable medicament delivery system or medical device can be used. For example, the medicament delivery system or the medical device can be an implant, e.g., an implant placed during or after bone surgery, a catheter, or a sustained-release drug delivery system.

In some embodiments, the present methods can further comprise assessing efficacy of the nanoparticle and/or the other active ingredient in preventing and/or treating a disease or disorder associated with a damaged or leaky vasculature in a subject. The efficacy of the nanoparticle and/or the other active ingredient in preventing and/or treating a disease or disorder associated with a damaged or leaky vasculature can be assessed by any suitable methods, e.g., in vitro and/or in vivo tests. For example, the present methods can be used for preventing and/or treating any suitable restenosis, and the efficacy of the nanoparticle and/or the other active ingredient can be assessed by any suitable measurement of restenosis, e.g., by imaging of restenosis, or by measuring restenosis as "Late Loss," percent diameter restenosis, binary restenosis, intima-to-media ratio (I/M), or luminal obliteration.

The composition used in the present methods can be administered to the subject via any suitable route of administration. In some embodiments, the nanoparticle used in the present methods, alone or in combination with other active ingredient(s), can be administered via oral, parenteral, rectal, nasal, topical, or ocular routes, or by inhalation. Exemplary parenteral administration can be via intravenous, intramuscular, intraperitoneal, intranasal, or subcutaneous route.

In another aspect, the present invention is directed to use of an effective amount of a nanoparticle for the manufacture of a medicament for preventing and/or treating (and/or related uses) a disease or disorder associated with a damaged or leaky vasculature in a subject, wherein said nanoparticle comprises: a) an inner core comprising a non-cellular material, b) an outer surface comprising a cellular membrane derived from a platelet; and optionally c) an agent for preventing said disease or disorder, treating said disease or disorder, diagnosing said disease or disorder, prognosing said disease or disorder and/or monitoring prevention or treatment of said disease or disorder.

C. Combinations for Decreasing or Neutralizing the Effect of a Toxin in a Subject In still another aspect, the present invention is directed to a combination for preventing and/or treating (and/or related uses) a disease or disorder associated with a damaged or leaky vasculature in a subject, which combination comprises an effective amount of a nanoparticle and an effective amount of a second prophylactic or therapeutic agent for preventing and/or treating a disease or disorder associated with a damaged or leaky vasculature in a subject, wherein said nanoparticle comprises: a) an inner core comprising a non-cellular material, b) an outer surface comprising a cellular membrane derived from a platelet; and optionally c) an agent for preventing said disease or disorder, treating said disease or disorder, diagnosing said disease or disorder, prognosing said disease or disorder and/or monitoring prevention or treatment of said disease or disorder. In some embodiments, the disease or disorder is not a disease or disorder disclosed in U.S. application Ser. No. 13/827,906, filed Mar. 14, 2013, international Application No. PCT/US2012/039411, filed May 24, 2012 and published as WO 2013/052167 A2 and U.S. provisional application Ser. No. 61/492,626, filed Jun. 2, 2011.

The present combination can be made, stored and/or used in any suitable formulation. In some embodiments, the present invention provides for a pharmaceutical composition comprising the above combination admixed with at least one pharmaceutically acceptable carrier or excipient. In other embodiments, the present invention provides for a method for preventing and/or treating a disease or disorder associated with a damaged or leaky vasculature in a subject, which method comprises administering, to a subject in need, or to cells of said subject, an effective amount of the above combination or pharmaceutical composition.

The above combination or pharmaceutical composition can be used to prevent and/or treat a disease or disorder associated with a damaged or leaky vasculature in any suitable subject. In some embodiments, the subject is a mammal. In some embodiments, the mammal is a human. In other embodiments, the manual is a non-human manual, including a pet, a farm animal, an economic animal, a sport animal and an experimental animal, such as a cat, a dog, a horse, a cow, an ox, a pig, a donkey, a sheep, a lamb, a goat, a mouse, a rabbit, a primate, including a monkey and a chimpanzee.

In some embodiments, the above combination or pharmaceutical composition can be used for preventing a disease or disorder associated with a damaged or leaky vasculature in a subject. In other embodiments, the above combination or pharmaceutical composition can be used for treating a disease or disorder associated with a damaged or leaky vasculature in a subject. The above combination or pharmaceutical composition can be used to prevent and/or treat a disease or disorder associated with a damaged or leaky vasculature in a subject to any suitable degree. For example, the above combination or pharmaceutical composition can be used to decrease or neutralize the effect of a disease or disorder associated with a damaged or leaky vasculature in a subject by at least 10%, 20%, 30%, 40%, 50%, 60%, 70%, 80%, 90%, 91%, 92%, 93%, 94%, 95%, 96%, 97%, 98%, 99% or more compared to a comparable untreated subject or to the same subject at an untreated stage.

The nanoparticle used in the above combination or pharmaceutical composition can comprise any suitable inner core. For example, the inner core of the nanoparticle can comprise a polymeric particle core, a silica particle core, or a metal, e.g., gold, particle core. Any suitable polymeric particle core can be used. In some embodiments, the polymeric particle core can comprise an optical shift property. In other embodiments, the polymeric particle core can comprise a metal, e.g., gold, iron oxide or a quantum dot. In still other embodiments, the inner core of the nanoparticle can comprise a biocompatible or a synthetic material, such as poly(lactic-c-glycolic acid) (PLGA), polylactic acid (PLA), polyglycolic acid (PGA), polycaprolactone (PCL), polylysine, and polyglutamic acid. In yet other embodiments, the inner core of the nanoparticle supports the outer surface.

The nanoparticle used in the above combination or pharmaceutical composition can comprise any suitable cellular membrane derived from a platelet. For example, the nanoparticle used in the above combination or pharmaceutical composition can comprise a plasma membrane derived from a platelet. In another example, the nanoparticle used in the above combination or pharmaceutical composition can comprise an intracellular membrane derived from a platelet.

The therapeutic agent, the prophylactic agent, the diagnostic or marker agent, the prognostic agent, the isolation agent, the monitoring agent, or a combination thereof, can be comprised in any suitable location in the above combination or pharmaceutical composition. For example, the therapeutic agent, the prophylactic agent, the diagnostic or marker agent, the prognostic agent, the isolation agent, the monitoring agent, or a combination thereof, can be comprised in the nanoparticle. In some embodiments, the therapeutic agent, the prophylactic agent, the diagnostic or marker agent, the prognostic agent, the isolation agent, the monitoring agent, or a combination thereof, can be comprised in a releasable cargo in the nanoparticle.

The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or cells of the subject, or by a change of a physical parameter surrounding the nanoparticle. The nanoparticle can comprise any suitable type of a releasable cargo. For example, the releasable cargo can be a metallic particle, a polymeric particle, a dendrimer particle, or an inorganic particle.

In some embodiments, the therapeutic agent, the prophylactic agent, the diagnostic or marker agent, the prognostic agent, the isolation agent, the monitoring agent, or a combination thereof, can be comprised in the above combination or pharmaceutical composition but outside the nanoparticle.

In some embodiments, the therapeutic agent is used for treating a disease or disorder associated with a damaged or leaky vasculature in a subject. In other embodiments, the prophylactic agent is used for preventing a disease or disorder associated with a damaged or leaky vasculature in a subject. In still other embodiments, the diagnostic or marker agent is used for diagnosing a disease or disorder associated with a damaged or leaky vasculature in a subject. In yet other embodiments, the prognosing or marker agent is used for prognostic a disease or disorder associated with a damaged or leaky vasculature in a subject. In yet other embodiments, the monitoring agent is used for monitoring prevention or treatment of a disease or disorder associated with a damaged or leaky vasculature in a subject. In yet other embodiments, the isolation agent is used for facilitating isolation and removal of a cell, tissue or organ associated with the damaged or leaky vasculature from the subject. The isolation agent can comprise any suitable material. In some embodiments, the isolation agent comprises a magnetic material, e.g., iron oxide.

The nanoparticle used in the above combination or pharmaceutical composition can have any suitable size. For example, the nanoparticle can have a diameter from about 10 nm to about 10 μm. In certain embodiments, the diameter of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm, or any sub-range within about 10 nm to about 10 μm, e.g., any range between any two of the above sizes.

The nanoparticle used in the above combination or pharmaceutical composition can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle used in the above combination or pharmaceutical composition substantially lacks constituents of the platelet from which the cellular membrane is derived. For example, the nanoparticle can lack 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the platelet from which the cellular membrane is derived.

In some embodiments, the nanoparticle used in the above combination or pharmaceutical composition substantially maintains the natural structural integrity or activity of the cellular membrane derived from the platelet or the constituents of the cellular membrane derived from the platelet. For example, the nanoparticle can retain 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity or activity for targeting a damaged or leaky vasculature in a subject.

In some embodiments, the nanoparticle used in the above combination or pharmaceutical composition is biocompatible or biodegradable. For example, the inner core of the nanoparticle comprises PLGA and the outer surface of the nanoparticle comprises a plasma membrane derived from the platelet.

The nanoparticle used in the above combination or pharmaceutical composition can have any suitable half-life in vivo. For example, the nanoparticle can have a half-life in blood circulation in vivo for at least from about 30 minutes to about 10 hours, e.g., about 1, 2, 3, 4, 5, 6, 7, 8, 9, 10 hours.

The outer surface of the nanoparticle used in the above combination or pharmaceutical composition can further comprise a synthetic membrane. In some embodiments, the nanoparticles used in the above combination or pharmaceutical composition comprise a mixture of nanoparticles that comprise an outer surface comprising a platelet cellular membrane and nanoparticles that comprise an outer surface comprising a synthetic membrane. The nanoparticles that comprise an outer surface comprising a synthetic membrane may or may not be capable of targeting a damaged or leaky vasculature in a subject. In some embodiments, both the nanoparticles that comprise an outer surface comprising a platelet cellular membrane and nanoparticles that comprise an outer surface comprising a synthetic membrane are capable of targeting a damaged or leaky vasculature in a subject. In other embodiments, the nanoparticles that comprise an outer surface comprising a platelet cellular membrane is capable of targeting a damaged or leaky vasculature in a subject, but the nanoparticles that comprise an outer surface comprising a synthetic membrane is not capable of targeting a damaged or leaky vasculature in a subject.

The composition used in the above combination or pharmaceutical composition can comprise the nanoparticles that comprise an outer surface comprising a platelet cellular membrane and nanoparticles that comprise an outer surface comprising a synthetic membrane in any suitable ratio. In some embodiments, the present composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a platelet cellular membrane. In other embodiments, the present composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a synthetic membrane. For example, the composition used in the above combination or pharmaceutical composition can comprise about 1-10% (w/w) of the nanoparticles that comprise an outer surface comprising a platelet cellular membrane and about 90-99% (w/w) of the nanoparticles that comprise an outer surface comprising a synthetic membrane, about 11-25% (w/w) of the nanoparticles that comprise an outer surface comprising a platelet cellular membrane and about 75-89% (w/w) of the nanoparticles that comprise an outer surface comprising a synthetic membrane, about 50% (w/w) of the nanoparticles that comprise an outer surface comprising a platelet cellular membrane and about 50% (w/w) of the nanoparticles that comprise an outer surface comprising a synthetic membrane, about 51-75% (w/w) of the nanoparticles that comprise an outer surface comprising a platelet cellular membrane and about 49-25% (w/w) of the nanoparticles that comprise an outer surface comprising a synthetic membrane, or about 90-100% (w/w) of the nanoparticles that comprise an outer surface comprising a platelet cellular membrane and about 0-10% (w/w) of the nanoparticles that comprise an outer surface comprising a synthetic membrane.

The composition used in the above combination or pharmaceutical composition can comprise the nanoparticles that comprise an outer surface comprising a hybrid membrane comprising a cellular membrane derived from a platelet and a synthetic membrane. In some embodiments, the outer surface of the nanoparticle can comprise a hybrid membrane comprising at least about 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w) of a cellular membrane derived from a platelet. In other embodiments, the outer surface of the nanoparticle can comprise a hybrid membrane comprising at least about 1% (w/w), 2% (w/w), 3% (w/w), 4% (w/w), 5% (w/w), 6% (w/w), 7% (w/w), 8% (w/w), 9% (w/w), 10% (w/w), 20c (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w) of a synthetic membrane. For example, the outer surface of the nanoparticle can comprise a hybrid membrane comprising about 5-10% (w/w) of a cellular membrane derived from a platelet and about 90-95% (w/w) of a synthetic membrane, about 11-25% (w/w) of a cellular membrane derived from a platelet and about 75-89% (w/w) of a synthetic membrane, about 50% (w/w) of a cellular membrane derived from a platelet and about 50% (w/w) of a synthetic membrane, about 51-75% (w/w) of a cellular membrane derived from a platelet and about 49-25% (w/w) of a synthetic membrane, or about 90-99% (w/w) of a cellular membrane derived from a platelet and about 1-10% (w/w) of a synthetic membrane.

In some embodiments, the nanoparticle used in the above combination or pharmaceutical composition substantially lacks immunogenicity to the subject, e.g., a mammal. For example, the cellular membrane can be derived from a platelet from the same species of the subject. In another example, the subject is a human and the cellular membrane is derived from a human platelet. In some embodiments, the cellular membrane can be derived from a platelet of the mammal to be treated. For example, the cellular membrane can be derived from a platelet of the human to be treated.

The above combination or pharmaceutical composition can be used for preventing and/or treating any suitable disease or disorder associated with a damaged or leaky vasculature in a subject. For example, the above combination or pharmaceutical composition can be used for preventing and/or treating a disease or disorder associated with a damaged vasculature in a subject. In another example, the above combination or pharmaceutical composition can be used for preventing and/or treating a disease or disorder associated with a leaky vasculature in a subject. In still another example, the above combination or pharmaceutical composition can be used for preventing and/or treating hemorrhage (bleeding), a cardiovascular disease or disorder, a disease or disorder associated with narrowing of a blood vessel, a tumor or a cancer that is associated with a damaged or leaky vasculature in a subject.

In some embodiments, the above combination or pharmaceutical composition can be used for preventing and/or treating hemorrhage associated with a damaged or leaky vasculature in a subject. The nanoparticle used in the above combination or pharmaceutical composition can comprise an agent for preventing the hemorrhage, treating the hemorrhage, diagnosing the hemorrhage, prognosing hemorrhage and/or monitoring prevention or treatment of the hemorrhage.

The above combination or pharmaceutical composition can be used for preventing and/or treating any suitable hemorrhage associated with a damaged or leaky vasculature in a subject. In some embodiments, the hemorrhage to be prevented and/or treated is internal hemorrhage or external hemorrhage. In other embodiments, the hemorrhage to be prevented and/or treated is class I hemorrhage, class II hemorrhage, class III hemorrhage or class IV hemorrhage. In still other embodiments, the hemorrhage to be prevented and/or treated is mouth hemorrhage, e.g., hematemesis or hemoptysis, anus hemorrhage, e.g., haematochezia, urinary tract hemorrhage, e.g., hematuria, upper head hemorrhage, e.g., intracranial hemorrhage, cerebral hemorrhage, cerebral hemorrhage, or subarachnoid hemorrhage, lungs hemorrhage, e.g., pulmonary hemorrhage, gynecologic hemorrhage, e.g., vaginal bleeding (such as postpartum bleeding or breakthrough bleeding), or ovarian bleeding, gastrointestinal hemorrhage, e.g., upper gastrointestinal bleeding, lower gastrointestinal bleeding, or occult gastrointestinal bleeding. In yet other embodiments, the hemorrhage to be prevented and/or treated is caused by a traumatic injury, e.g., an abrasion, an excoriation, a hematoma, a laceration, an incision, a puncture wound, a contusion, a crushing injury or a ballistic trauma. In yet other embodiments, the hemorrhage to be prevented and/or treated is caused by a medical condition. For example, the hemorrhage to be prevented and/or treated can be caused by an intravascular change, e.g., increase or decrease of blood pressure or decrease of the level of a clotting factor, an intramural change, e.g., aneurysm, aortic dissection, arteriovenous malformation or vasculitis, or an extravascular change, e.g., *H. pylori* infection, brain abscess or a brain tumor.

In some embodiments, the hemorrhage to be prevented and/or treated is caused by a medication. For example, the hemorrhage to be prevented and/or treated can be caused by a nonsteroidal anti-inflammatory drug, e.g., aspirin or ibuprofen. The nanoparticle used in the above combination or pharmaceutical composition can comprise an agent for antagonizing the effect of the nonsteroidal anti-inflammatory drug.

In some embodiments, the hemorrhage to be prevented and/or treated is caused by a deficiency in blood coagulation. For example, the hemorrhage to be prevented and/or treated is haemophilia A caused by deficiency of Factor VIII. The nanoparticle used in the above combination or pharmaceutical composition can comprise an effective amount of Factor VIII. In another example, the hemorrhage to be prevented and/or treated is haemophilia B caused by deficiency of Factor IX. The nanoparticle used in the above combination or pharmaceutical composition can comprise an effective amount of Factor IX. In still another example, the hemorrhage to be prevented and/or treated is caused by an antibody to Factor VIII. The nanoparticle used in the above combination or pharmaceutical composition can comprise an effective amount of an agent for antagonizing the effect of the antibody to Factor VIII. In yet another example, the hemorrhage to be prevented and/or treated is Von Willebrand disease caused by deficiency of the "von Willebrand" factor. The nanoparticle used in the above combination or pharmaceutical composition can comprise an effective amount of "von Willebrand" factor. In yet another example, the hemorrhage to be prevented and/or treated is caused by deficiency of Factor VII or Factor XIII. The nanoparticle used in the above combination or pharmaceutical composition can comprise an effective amount of Factor VII or Factor XIII. In yet another example, the hemorrhage to be prevented and/or treated is warfarin-related bleeding caused by administration of an antibiotic. The nanoparticle used in the above combination or pharmaceutical composition can comprise an effective amount of an agent for antagonizing the effect of the warfarin or the antibiotic, or an effective amount of vitamin K.

In some embodiments, the hemorrhage to be prevented and/or treated occurs during or after a surgery. In some embodiments, the hemorrhage to be prevented and/or treated occurs during or after a warfare, a terror attack, a suicide attempt or an accident.

In some embodiments, the above combination or pharmaceutical composition can be used for preventing and/or treating a cardiovascular disease or disorder associated with a damaged or leaky vasculature in a subject. The nanoparticle used in the above combination or pharmaceutical composition can comprise an agent for preventing the cardiovascular disease or disorder, treating the cardiovascular disease or disorder, diagnosing the cardiovascular disease or disorder, prognosing the cardiovascular disease or disorder and/or monitoring prevention or treatment of the cardiovascular disease or disorder.

The above combination or pharmaceutical composition can be used for preventing and/or treating any suitable cardiovascular disease or disorder associated with a damaged or leaky vasculature in a subject. In some embodiments, the cardiovascular disease or disorder to be prevented and/or treated is a coronary artery disease (CAD) (also known as ischemic heart disease (IHD), atherosclerotic heart disease, atherosclerotic cardiovascular disease or coronary heart disease), a stroke (also known as cerebrovascular accident (CVA), cerebrovascular insult (CVI), or brain attack), a hypertensive heart disease, a rheumatic heart disease (RHD), an atrial fibrillation (AF or A-fib), an aortic aneurysm, a cardiomyopathy, a congenital heart defect (CHD), an endocarditis, or a peripheral artery disease (PAD). In other embodiments, the cardiovascular disease or disorder to be prevented and/or treated is associated with atherosclerosis (also known as arteriosclerotic vascular disease or ASVD).

The nanoparticle used in the above combination or pharmaceutical composition can comprise an effective amount of a medication for preventing and/or treating the cardiovascular disease or disorder. Any suitable medication can be used. For example, the medication for preventing and/or treating the cardiovascular disease or disorder can be an ACE inhibitor, an angiotensin II receptor blocker, an anti-arrythmic, an antiplatelet medication, aspirin, a beta-blocker, a clot buster (thrombolytic), Coumadin, digoxin, a statin, a diuretic and a vasodilator.

In some embodiments, the above combination or pharmaceutical composition can be used for preventing and/or treating a disease or disorder associated with narrowing of a blood vessel in a subject. The nanoparticle used in the above combination or pharmaceutical composition can comprise an agent for preventing the disease or disorder associated with narrowing of a blood vessel, treating the disease or disorder associated with narrowing of a blood vessel, diagnosing the disease or disorder associated with narrowing of a blood vessel, prognosing disease or disorder associated with narrowing of a blood vessel and/or monitoring prevention or treatment of the disease or disorder associated with narrowing of a blood vessel.

The above combination or pharmaceutical composition can be used for preventing and/or treating any suitable a disease or disorder associated with narrowing of a blood vessel in a subject. In some embodiments, the disease or disorder associated with narrowing of a blood vessel to be prevented and/or treated is restenosis. The above combination or pharmaceutical composition can be used for preventing and/or treating any suitable restenosis. For example, the restenosis to be prevented and/or treated is restenosis of an artery or restenosis of a blood vessel within an organ. In another example, the restenosis to be prevented and/or treated is an adverse event of an endovascular procedure, e.g., a vascular surgery, a cardiovascular (heart) surgery or an angioplasty (or balloon angioplasty).

The nanoparticle used in the above combination or pharmaceutical composition can comprise an effective amount of an agent for inhibiting or reducing tissue growth that contributes to the restenosis. Any suitable agent for inhibiting or reducing tissue growth that contributes to the restenosis can be used. In some embodiments, an agent that inhibits or reduces neointimal hyperplasia can be used. Exemplary agent for inhibiting or reducing neointimal hyperplasia can be an agent for anti-inflammatory treatment, e.g., IL-10, an agent for nitric oxide-based treatment, a glucagon-like peptide-1 receptor (GLP-1) agonist, e.g., exendin-4, or a mitotic inhibitor. Exemplary mitotic inhibitor can be a taxane, e.g., paclitaxel or docetaxel, a vinca alkaloid, e.g., vinblastine, vincristine, vindesine or vinorelbine, colchicine, podophyllotoxin, podophyllin, or griseofulvin. In other embodiments, the restenosis to be prevented and/or treated is coronary restenosis and the nanoparticle comprises an effective amount of docetaxel.

In some embodiments, the nanoparticle used in the above combination or pharmaceutical composition can comprise an effective amount of an agent for pro-angiogenic therapy. The agent can be used for gene-therapy or protein-therapy. Any suitable pro-angiogenic agent can be used. For example, the pro-angiogenic agent can be fibroblast growth factor 1 (FGF-1) or a polynucleotide sequence that encodes FGF-1.

In some embodiments, the above combination or pharmaceutical composition can be used for preventing and/or treating tumor or a cancer associated with a damaged or leaky vasculature in a subject. The nanoparticle used in the above combination or pharmaceutical composition can comprise an agent for preventing the tumor or cancer, treating the tumor or cancer, diagnosing the tumor or cancer, prognosing the tumor or cancer and/or monitoring prevention or treatment of the tumor or cancer.

The above combination or pharmaceutical composition can be used for preventing and/or treating any suitable tumor or cancer associated with a damaged or leaky vasculature in a subject. In some embodiments, the tumor or cancer associated with a damaged or leaky vasculature to be prevented and/or treated can be sarcoma, epidermoid cancer, fibrosarcoma, cervical cancer, gastric carcinoma, skin cancer, leukemia, lymphoma, lung cancer, non-small cell lung cancer, colon cancer, CNS cancer, melanoma, ovarian cancer, renal cancer, prostate cancer, breast cancer, liver cancer, head and neck cancers, or pancreatic cancer.

In some embodiments, the tumor or cancer associated with a damaged or leaky vasculature to be prevented and/or treated is associated with tumor angiogenesis. The nanoparticle used in the above combination or pharmaceutical composition can comprise an effective amount of an angiogenesis inhibitor. Any suitable angiogenesis inhibitor can be used. Exemplary angiogenesis inhibitor can be angiostatin, endostatin, tumstatin or an antibody against an angiogenesis stimulator, e.g., vascular endothelial growth factor (VEGF). The angiogenesis inhibitor can be used for gene-therapy or protein-therapy.

In some embodiments, the above combination or pharmaceutical composition can further comprise administering a pharmaceutically acceptable carrier or excipient to the subject.

The above combination or pharmaceutical composition can be administered using any suitable delivery mechanisms or techniques. In some embodiments, the above combination or pharmaceutical composition can be administered alone. In other embodiments, the above combination or pharmaceutical composition can be administered with a pharmaceutically acceptable carrier or excipient. In still other embodiments, the above combination or pharmaceutical composition can be administered via a medicament delivery system or a medical device. Any suitable medicament delivery system or medical device can be used. For example, the medicament delivery system or the medical device can be an implant, e.g., an implant placed during or after bone surgery, a catheter, or a sustained-release drug delivery system.

The above combination or pharmaceutical composition can be administered to the subject via any suitable route of administration. In some embodiments, the above combination or pharmaceutical composition can be administered via oral, parenteral, rectal, nasal, topical, or ocular routes, or by inhalation. Exemplary parenteral administration can be via intravenous, intramuscular, intraperitoneal, intranasal, or subcutaneous route.

D. Pharmaceutical Compositions and Administration Routes

The pharmaceutical compositions comprising the nanoparticles, alone or in combination with other active ingredient(s), described herein may further comprise one or more pharmaceutically-acceptable excipients. A pharmaceutically-acceptable excipient is a substance that is non-toxic and otherwise biologically suitable for administration to a subject. Such excipients facilitate administration of the nanoparticles, alone or in combination with other active ingredient(s), described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the various embodiments are sterile compositions. Pharmaceutical compositions may be prepared using compounding techniques known or that become available to those skilled in the art.

Sterile compositions are within the present disclosure, including compositions that are in accord with national and local regulations governing such compositions.

The pharmaceutical compositions and the nanoparticles, alone or in combination with other active ingredient(s), described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. The nanoparticles, alone or in combination with other active ingredient(s), described herein, and preferably in the form of a pharmaceutical composition, may be administered by a suitable route of delivery, such as oral, parenteral, rectal, nasal, topical, or ocular routes, or by inhalation. In some embodiments, the compositions are formulated for intravenous or oral administration.

For oral administration, the nanoparticles, alone or in combination with another active ingredient, may be provided in a solid form, such as a tablet or capsule, or as a solution, emulsion, or suspension. To prepare the oral compositions, the nanoparticles, alone or in combination with other active ingredient(s), may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water: preservatives (for example, methyl or propyl p-hydroxybenzoate or sorbic acid); wetting agents such as lecithin; and, if desired, flavoring or coloring agents.

The compositions may be formulated for rectal administration as a suppository. For parenteral use, including intravenous, intramuscular, intraperitoneal, intranasal, or subcutaneous routes, the nanoparticles, alone or in combination with other active ingredient(s), may be provided in sterile aqueous solutions or suspensions, buffered to an appropriate pH and isotonicity or in parenterally acceptable oil. Suitable aqueous vehicles can include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For nasal, inhaled, or oral administration, the nanoparticles, alone or in combination with other active ingredient(s), may be administered using, for example, a spray formulation also containing a suitable carrier.

For topical applications, the nanoparticles, alone or in combination with other active ingredient(s), are preferably formulated as creams or ointments or a similar vehicle suitable for topical administration. For topical administration, the nanoparticles, alone or in combination with other active ingredient(s), may be mixed with a pharmaceutical carrier at a concentration of about 0.1% to about 10% of drug to vehicle. Another mode of administering the nanoparticles, alone or in combination with other active ingredient(s), may utilize a patch formulation to effect transdermal delivery.

In certain embodiments, the present disclosure provides a pharmaceutical composition comprising the nanoparticles, alone or in combination with other active ingredient(s), and methylcellulose. In certain embodiments, methylcellulose is in a suspension of about 0.1, 0.2, 0.3, 0.4, or 0.5 to about 1%, In certain embodiments, methylcellulose is in a suspension of about 0.1 to about 0.5, 0.6, 0.7, 0.8, 0.9, or 1%, In certain embodiments, methylcellulose is in a suspension of about 0.1 to about 1%, In certain embodiments, methylcellulose is in a suspension of about 0.1, 0.2, 0.3, 0.4, 0.5, 0.6, 0.7, 0.8, 0.8, or 1%, In certain embodiments, methylcellulose is in a suspension of about 0.5%.

F. Example 1. Nanoparticle Biointerfacing Via Platelet Membrane Cloaking

In one aspect, the invention relates to the preparation of polymeric nanoparticles enclosed in the plasma membrane of human platelets, which are a unique population of cellular fragments that adhere to a variety of disease-relevant substrates[4-7]. The resulting nanoparticles possess a right-side-out unilamellar membrane coating functionalized with immunomodulatory and adhesion antigens associated with platelets. As compared to uncoated particles, the platelet membrane-cloaked nanoparticles have reduced cellular uptake by macrophage-like cells and are absent of particle-induced complement activation in autologous human plasma. The cloaked nanoparticles also display platelet-mimicking properties such as selective adhesion to damaged human and rodent vasculatures as well as enhanced binding to platelet-adhering pathogens. In an experimental rat model of coronary restenosis and a mouse model of systemic bacterial infection, docetaxel and vancomycin, respectively, show enhanced therapeutic efficacy when delivered by the platelet-mimetic nanoparticles. The multifaceted biointerfacing enabled by the platelet membrane cloaking method provides a new approach in developing functional nanoparticles for disease-targeted delivery.

Figure 4A:
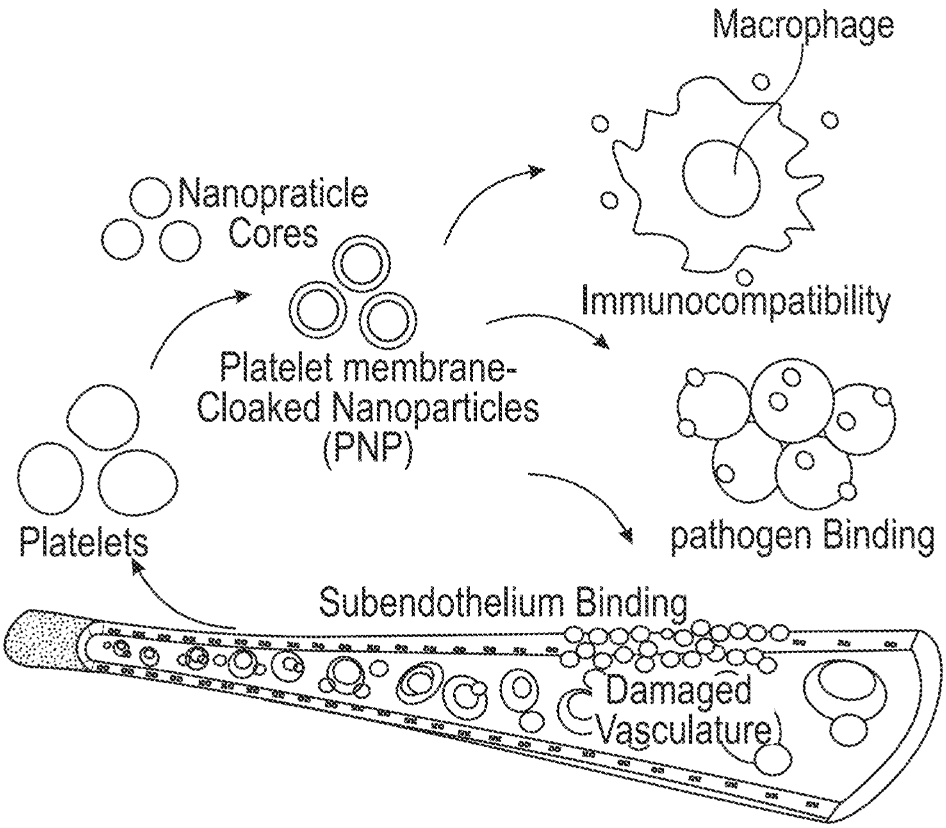
FIGS. 4A-4B.

Owing to their role as circulating sentinels for vascular damage as well as for invasive microorganisms, platelets have inspired the design of many functional nanocarriers[8-13]. The multitude of platelet functions stem from a unique set of surface moieties responsible for immune evasion[14,15], subendothelium adhesion[5,16], and pathogen imteractions[6,7]. By adopting a recently developed cell membrane cloaking technique[17,19], the preparation of platelet membrane-cloaked nanoparticles (PNPs) consisting of a biodegradable polymeric nanoparticle core shielded entirely in the plasma membrane of human platelets is demonstrated. Several inherent platelet properties, including immunocompatibility, binding to injured vasculature, and pathogen adhesion, as well as their therapeutic implications, were studied (FIG. 4A).

Figure 1C:
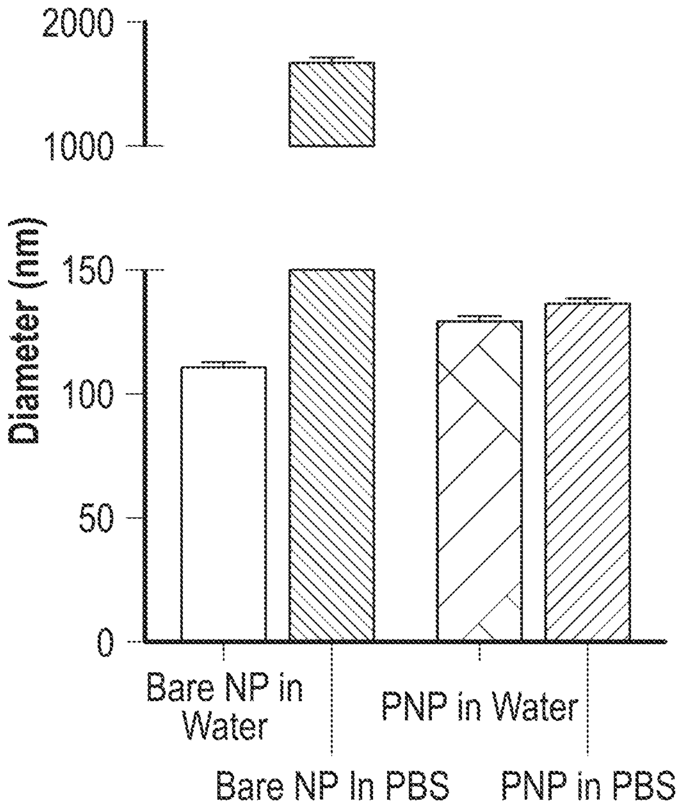
Figure 1D:
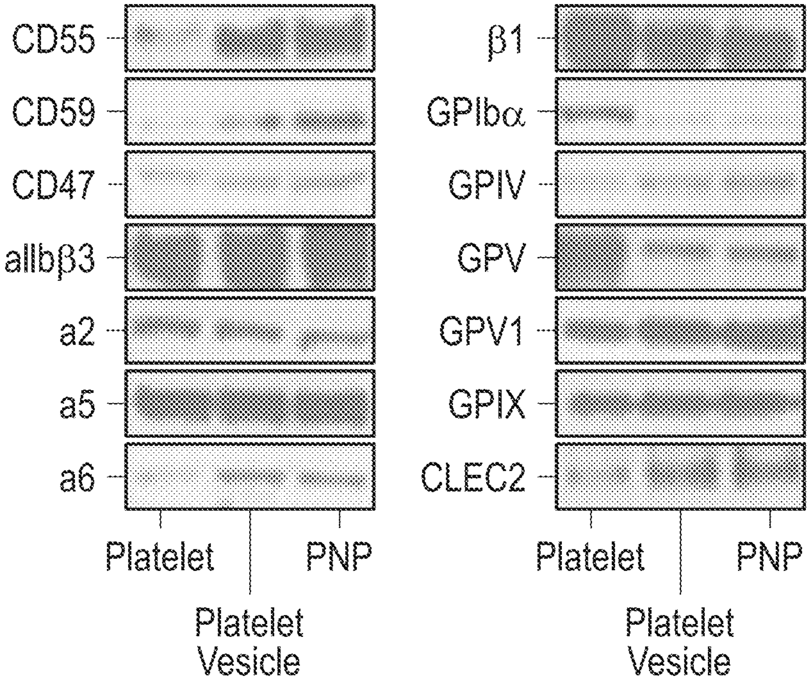
Figure 1E:
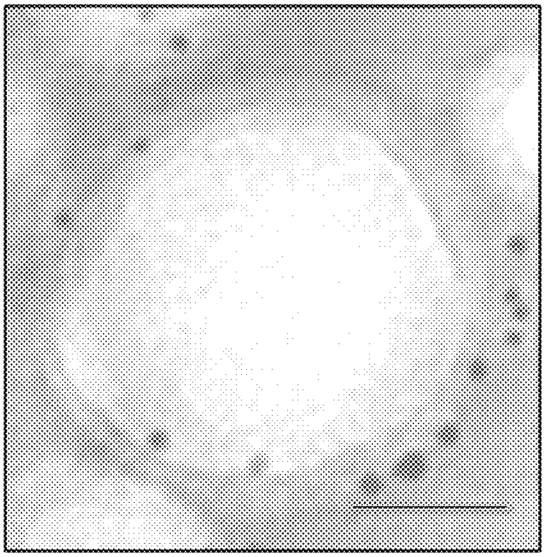
Figure 1F:
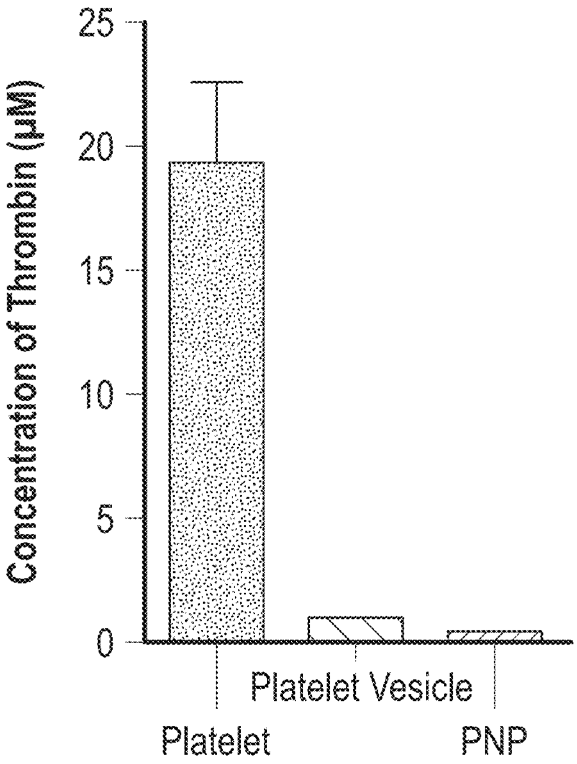
Figure 1G:
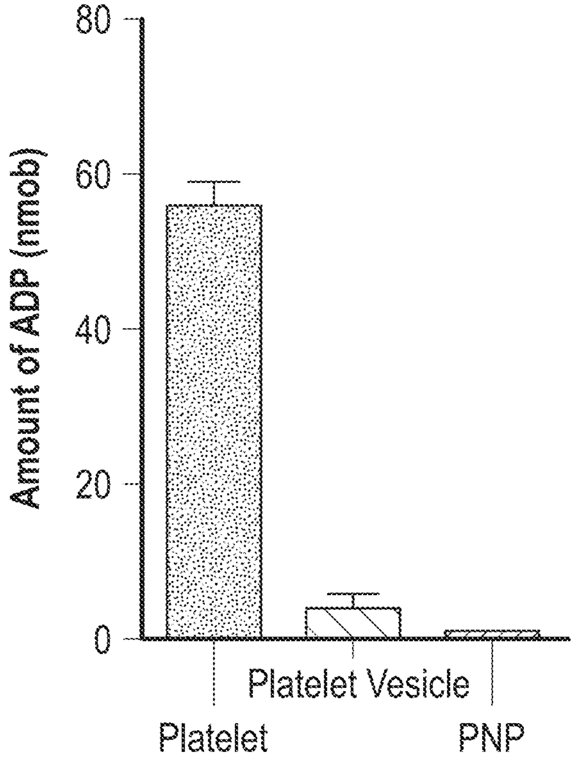
Figure 1H:
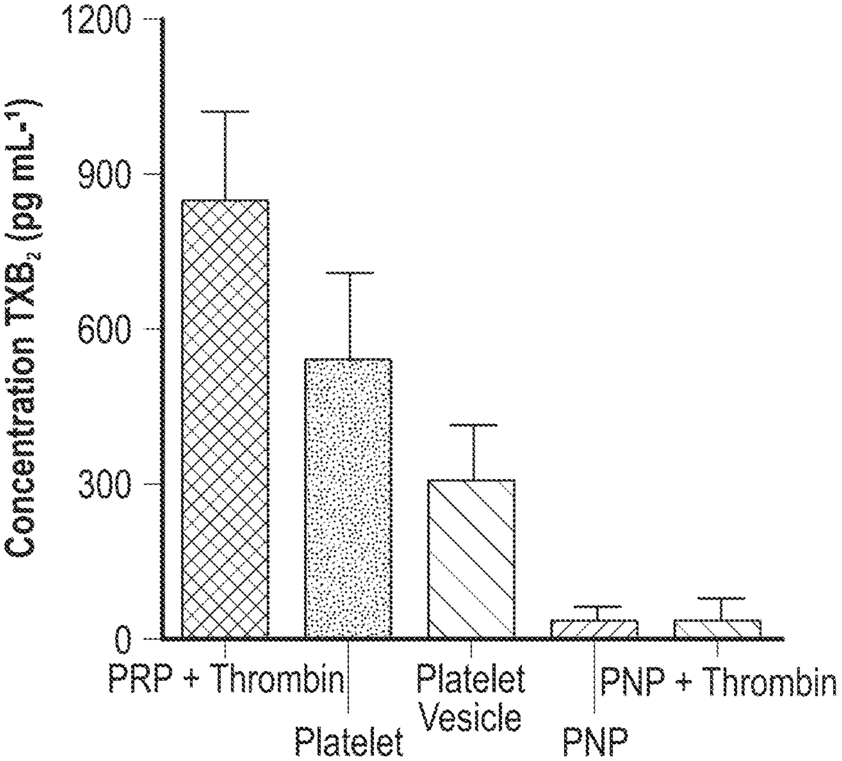
Figure 1I:
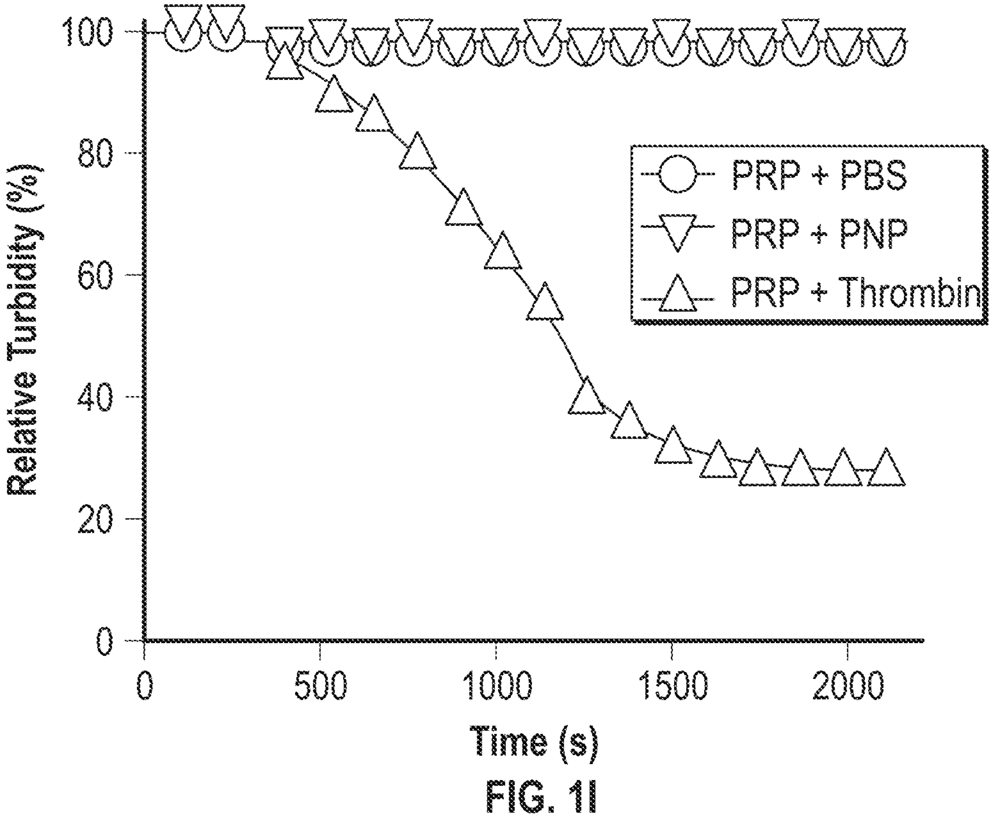
Figure 4B:
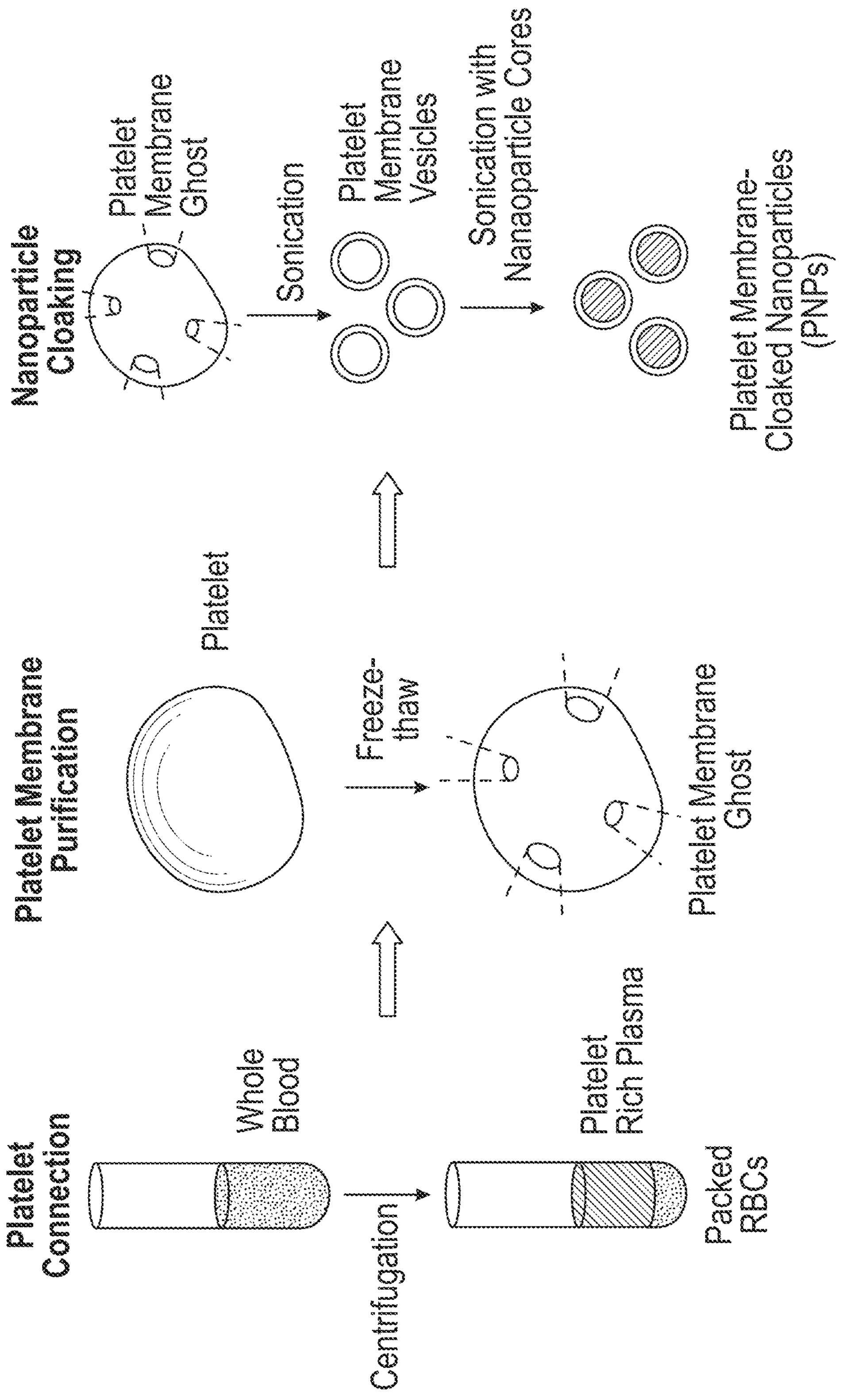
Figure 5A:
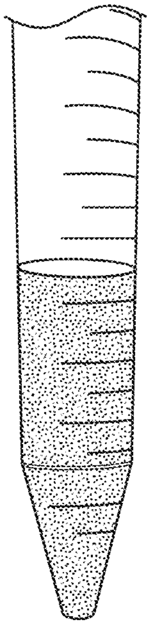
FIGS. 5A-5H show PNP preparation and storage.
Figure 5B:
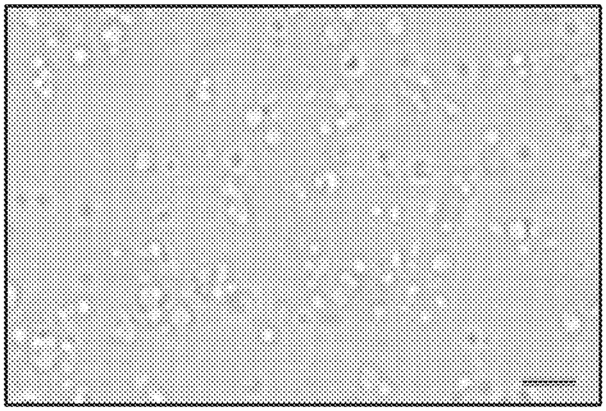
Figure 5C:
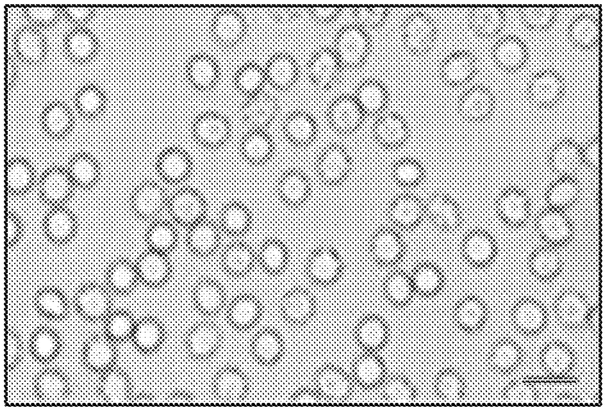
Figure 5D:
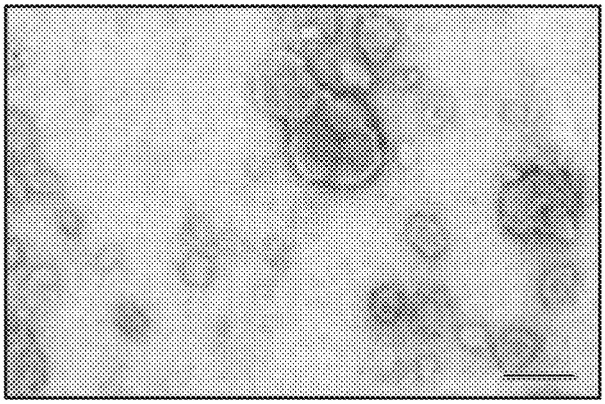
Figure 5E:
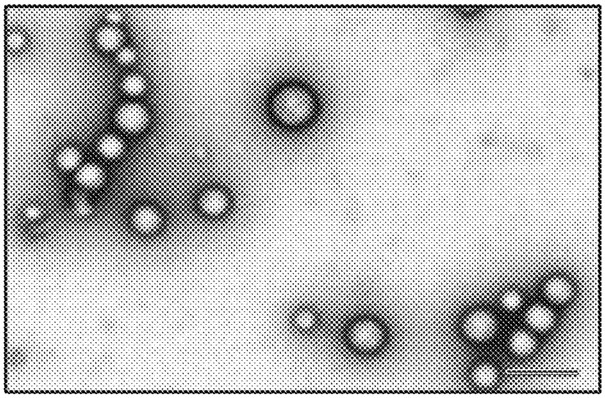
Figure 5F:
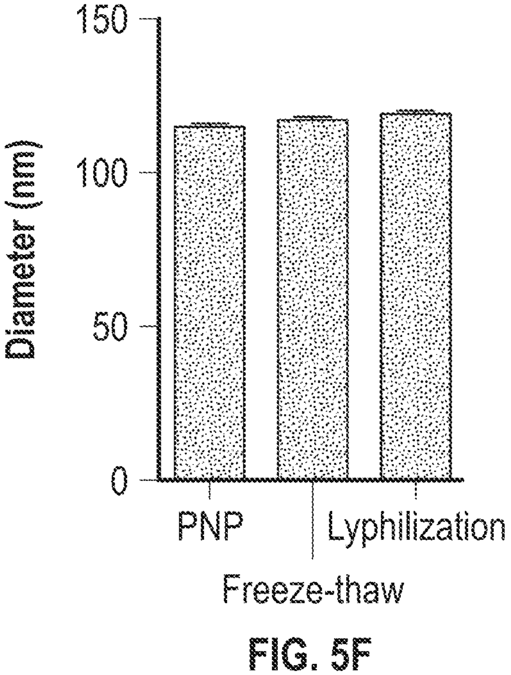
Figure 5G:
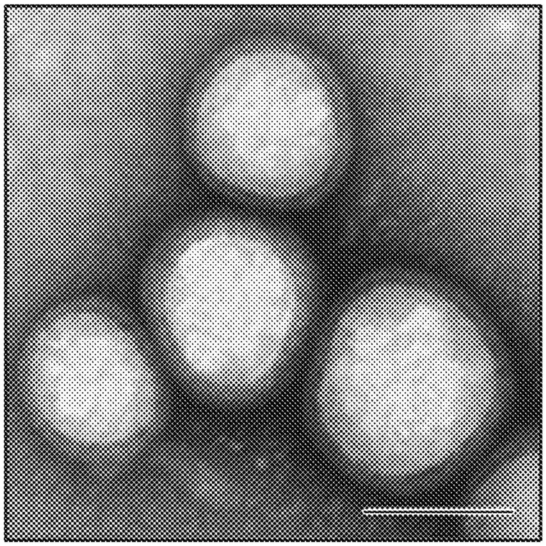
Figure 5H:
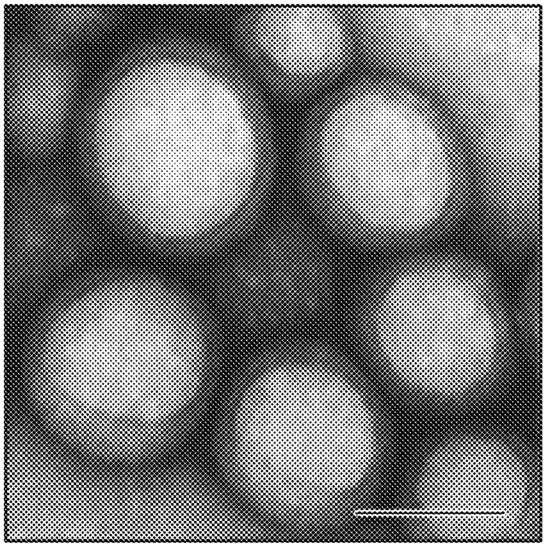
Figure 6:
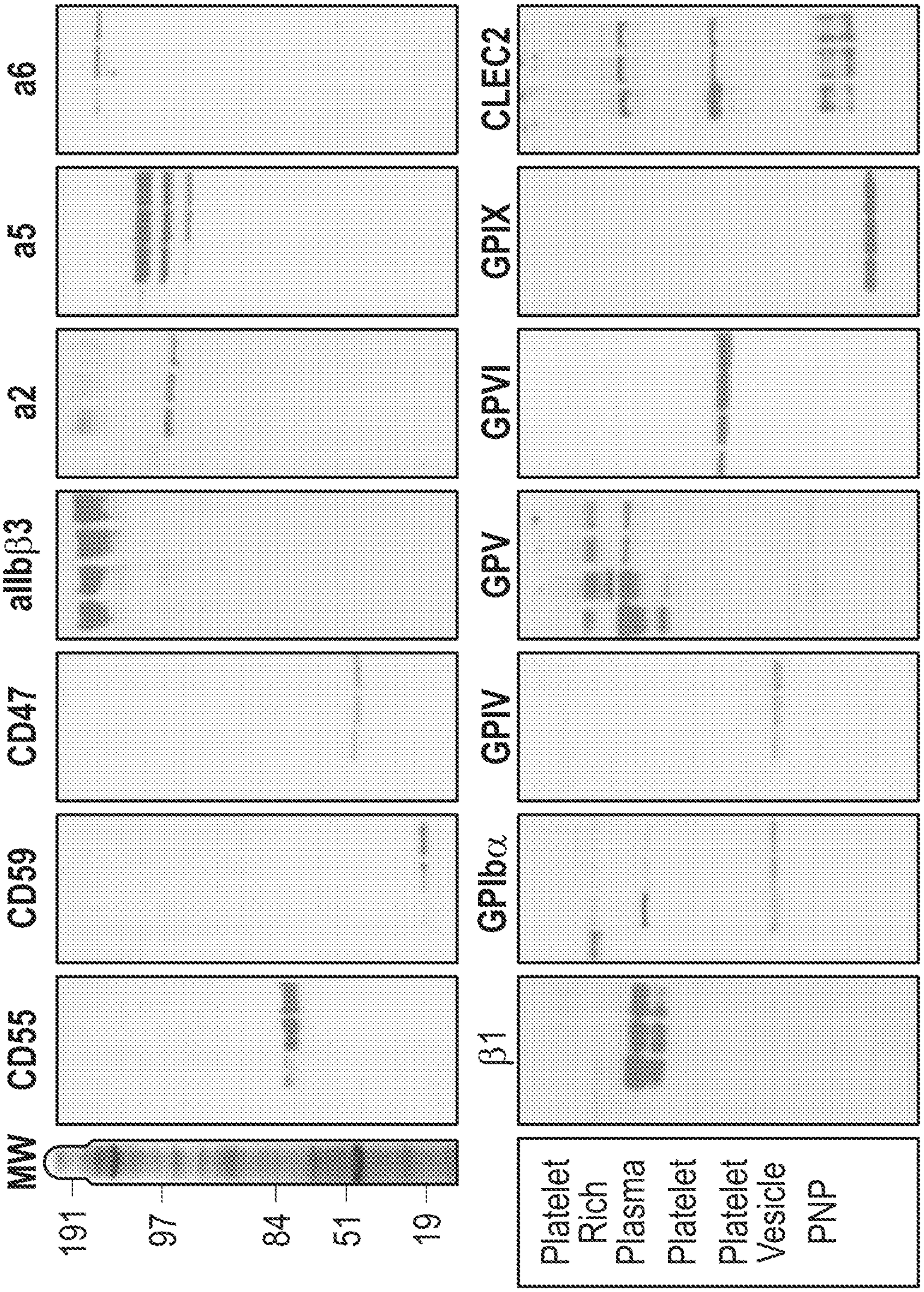
FIG. 6 shows overall protein content on PNPs resolved by western blotting. Primary platelet membrane protein/protein subunits such as CD47, CD55, CD59, αIIbβ3, α2, α5, α6, β1, GPIbα, GPIV, GPV, GPVI, GPIX, and CLEC-2 were monitored in platelet rich plasma, platelets, platelet vesicles, and PNPs. Each sample was normalized to equivalent overall protein content prior to western blotting.
Figure 7A:
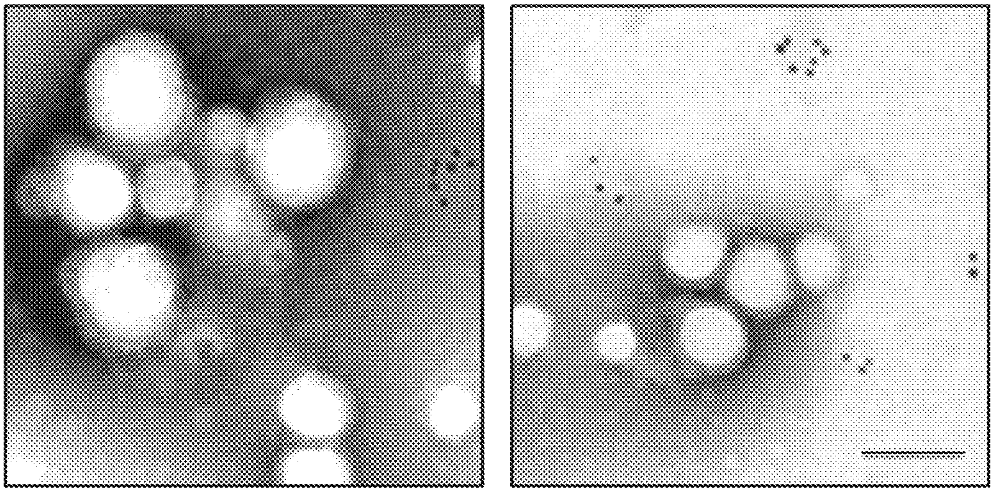
FIGS. 7A-7D show a platelet membrane sidedness on PNPs.
Figure 7B:
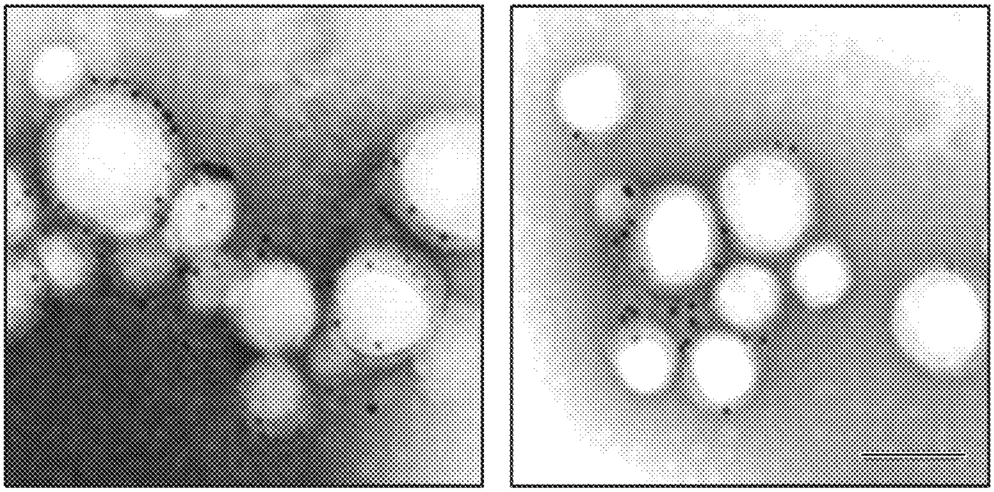
Figure 7C:
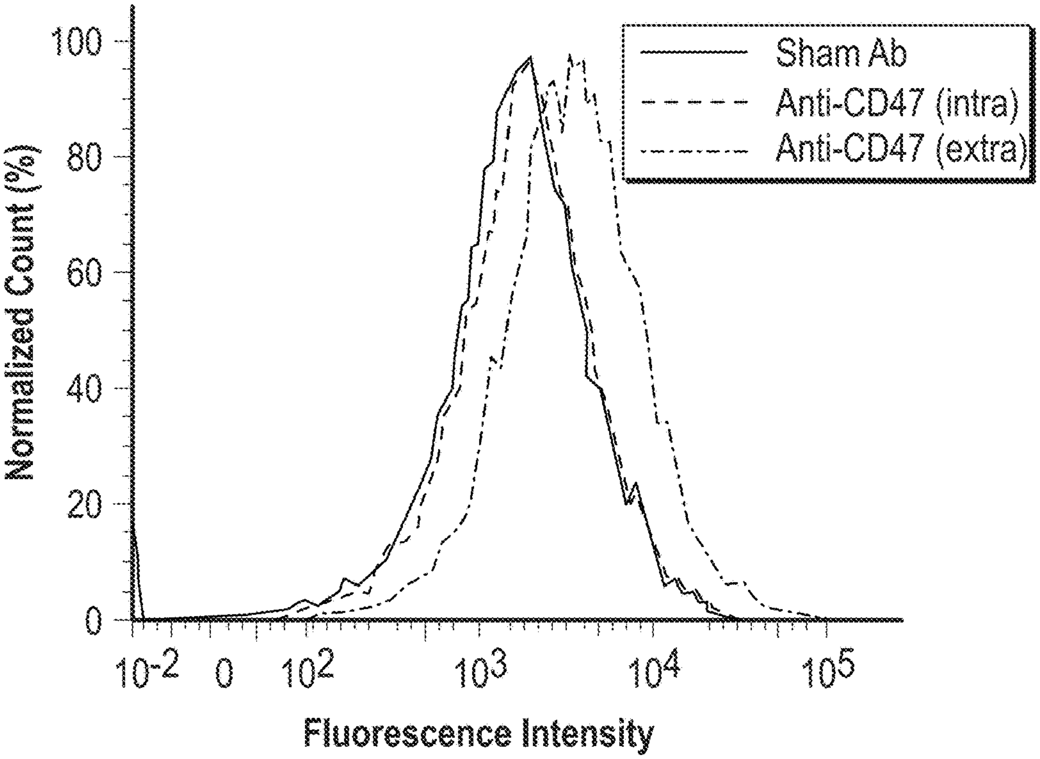
Figure 7D:
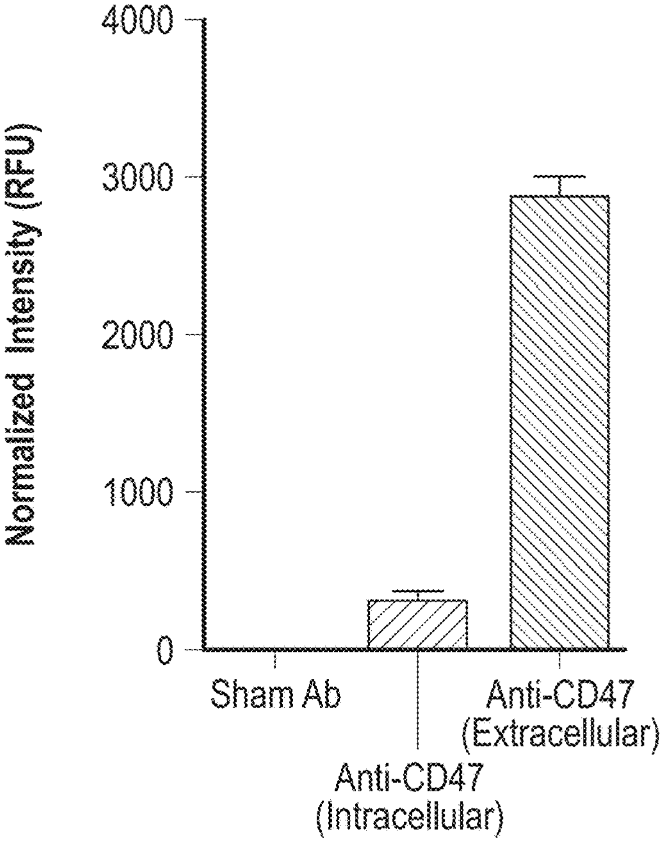
Figure 8A:
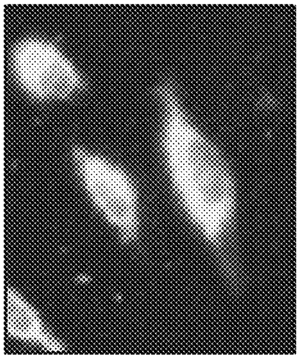
FIGS. 8A-8F show collagen-coated tissue culture slides seeded with human umbilical vein endothelial cells (HUVECs) were incubated with PNP solution for 30 sec. Fluorescence microscopy samples demonstrate differential PNP adherence to exposed collagen versus covered endothelial surfaces.
Figure 8B:
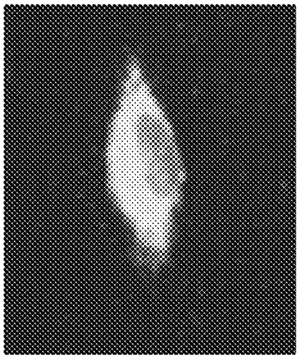
Figure 8C:
Figure 8D:
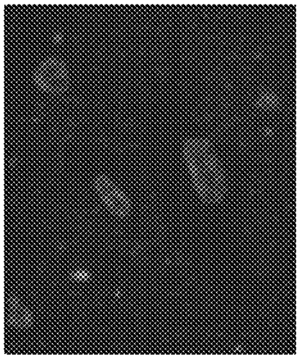
Figure 8E:
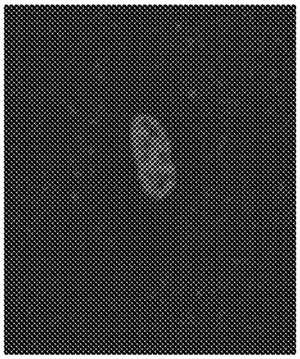
Figure 8F:
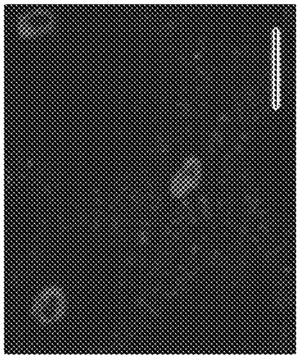
Figure 8G:
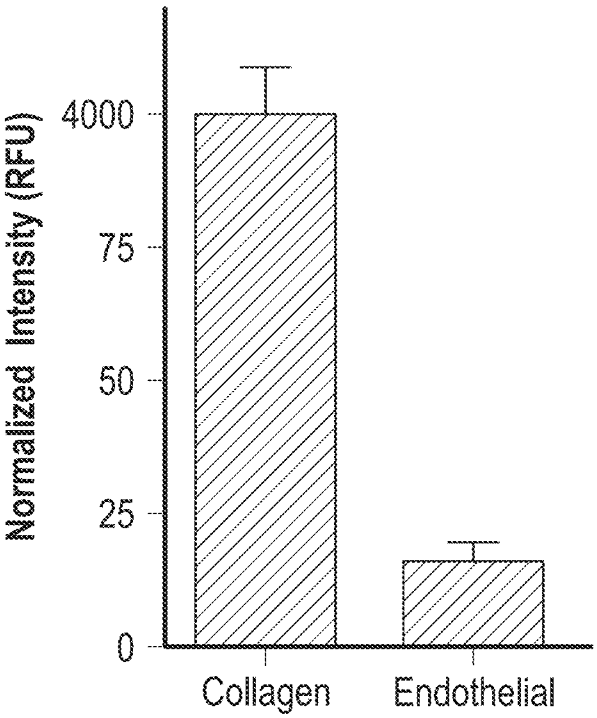
FIG. 8G shows fluorescence quantification of PNP per unit area on collagen and endothelial surfaces. Bars represent means±SD (n=10). (h,i) PNP adherence to arterial extracellular matrix (ECM) as visualized by SEM.
Figure 8H:
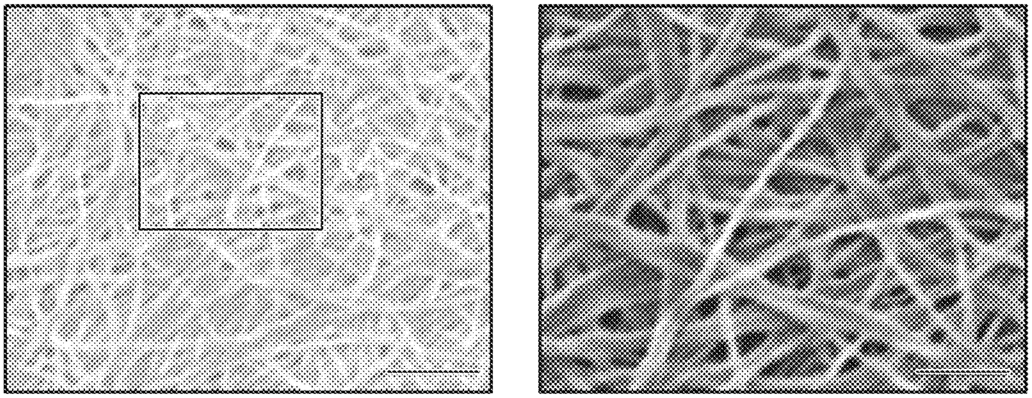
FIG. 8H shows SEM images of the ECM of a decellularized human umbilical cord artery. Left: Scale bar=1 μm; Right: Scale bar=500 nm.
Figure 8I:
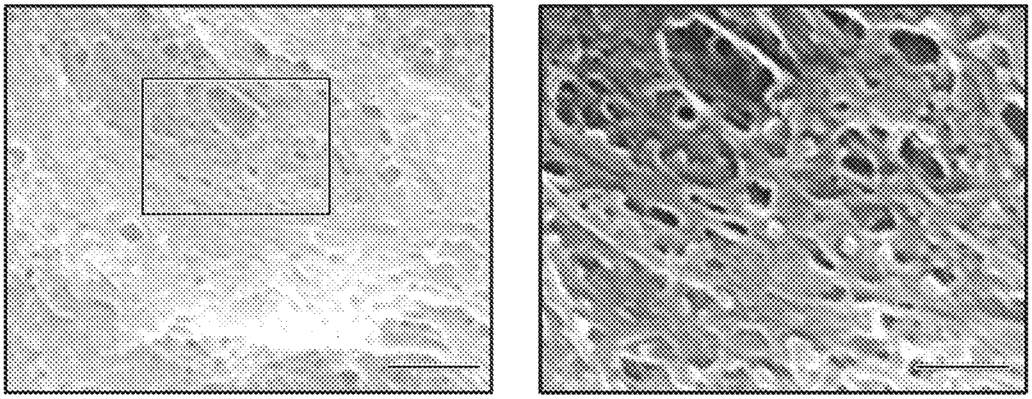
FIG. 8I shows SEM images of the ECM of a decellularized human umbilical cord artery following PNP incubation. Left: Scale bar=1 μm: Right: Scale bar=500 nm.

PNPs were prepared by fusing plasma membranes derived from human platelets with 100 nm poly(lactic-co-glycolic acid) (PLGA) nanoparticles. Platelet-rich plasma collected from human blood was first mixed with EDTA, which prevents platelet aggregation by deactivating fibrinogen-binding integrin $\alpha$IIb$\beta$3[20]. Platelets were then processed for nanoparticle membrane cloaking (FIG. 4B). Physicochemical characterizations revealed that the final PNPs were approximately 15 nm larger than the uncoated PLGA nanoparticles (bare NPs) and possessed an equivalent surface charge to that of platelet and platelet membrane-derived vesicles (platelet vesicles) (FIG. 1*a*). Transmission electron microscopy (TEM) visualization of platelet vesicles and PNPs showed the formation of distinctive nanoparticulates and consistent unilamellar membrane coatings over the polymeric cores (FIG. 1B and FIGS. 5A-5H). Improved colloidal stability was observed with the PNPs compared to bare NPs (FIG. 1C), which is attributable to the stabilizing effect by the plasma membrane's hydrophilic surface glycans[21]. Translocation of platelet membrane protein content, including immunomodulatory proteins, CD47, CD55, and CD59[14,15], integrin components, $\alpha$IIb$\beta$3, $\alpha$2, $\alpha$5, $\alpha$6, and $\beta$1, and other transmembrane proteins, GPIb$\alpha$, GPIV, GPV, GPVI, GPIX, and CLEC-2[5,16], onto the nanoparticles was verified via western blotting (FIG. 1D and FIG. 6). The majority of the membrane proteins were largely retained with the exception of GPIb$\alpha$ and GPV, which showed noticeable alterations attributable to their susceptibility to protease cleavage upon platelet perturbation[22]. A right-side-out membrane orientation on the PNPs was verified using both immunogold staining and flow cytometric analysis with antibodies targeting either the intracellular or extracellular domain of CD47 (FIG. 1E and FIGS. 7A-7D). Pro-thrombotic, platelet-activating molecules such as thrombin, ADP, and thromboxane were removed in the PNP formulation (FIGS. 1F-1H), thereby permitting PNP administration with little risk of a thrombotic response (FIG. 1I).

Figure 2A:
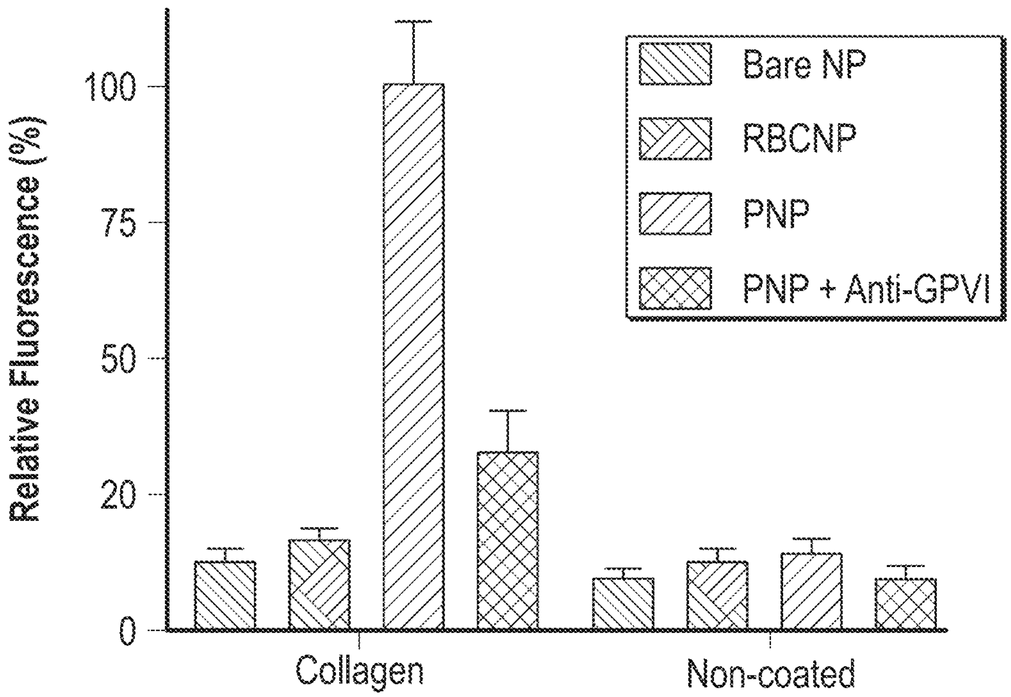
FIGS. 2A-2F show collagen binding and immunocompatibility.
Figure 2B:
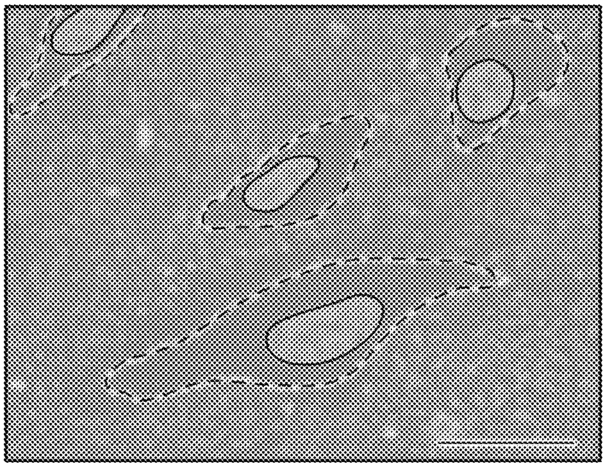
Figure 2C:
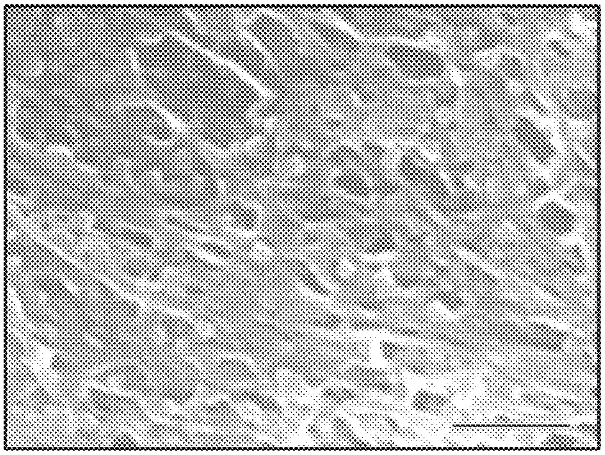

PNPs' platelet-mimicking functionalities were first studied via the particles' binding to human type IV collagen, a primary subendothelial component[23]. Fluorescently labeled PNPs, along with bare NPs and red blood cell membrane-cloaked nanoparticles (RBCNPs), were incubated on collagen-coated plates. The platelet membrane cloak significantly enhanced particle retention as compared to bare NPs and RBCNPs (FIG. 2*a*), indicating that the collagen adhesion was membrane type specific. Reduced PNP retention on non-collagen coated plates and in the presence of anti-GPVI antibodies supports a specific collagen/platelet membrane interaction attributable to the presence of membrane glycoprotein receptors for collagen[16] (Extended Data FIG. 3). Further examination of PNP's differential binding to endothelial and collagen surfaces was performed using collagen-coated tissue culture slides seeded with human umbilical vein endothelial cells (HUVECs). PNPs adhered primarily outside of areas encompassed by the cells (FIG. 2*b* and Extended Data FIG. 5*a-g*). In addition, the PNPs were incubated with the extracellular matrix derived from decellularized human umbilical cord arteries. Following PBS washes, scanning electron microscopy (SEM) revealed a significant number of PNPs remaining on the fibrous structures on the luminal side of the artery (FIG. 2*c* and Extended Data FIG. 5*h,i*).

Figure 2D:
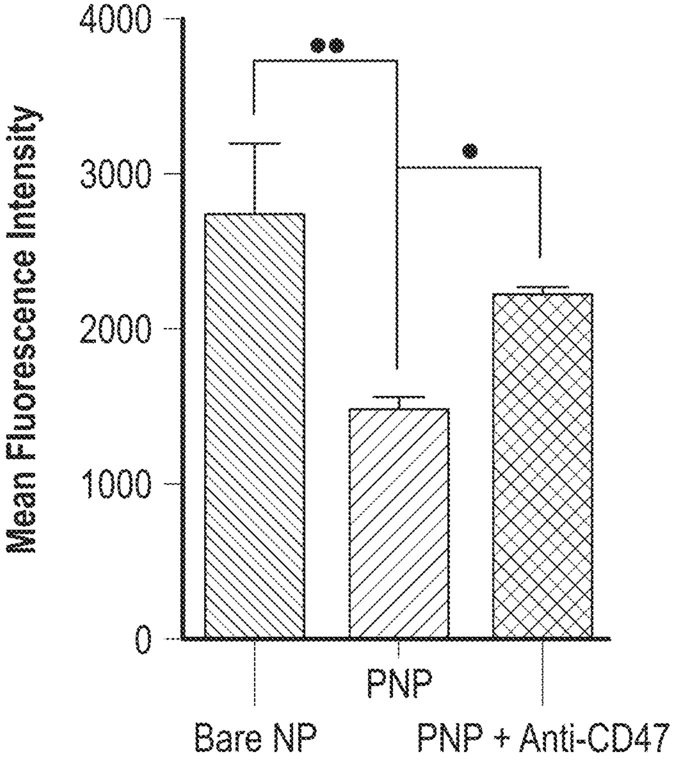
Figure 2E:
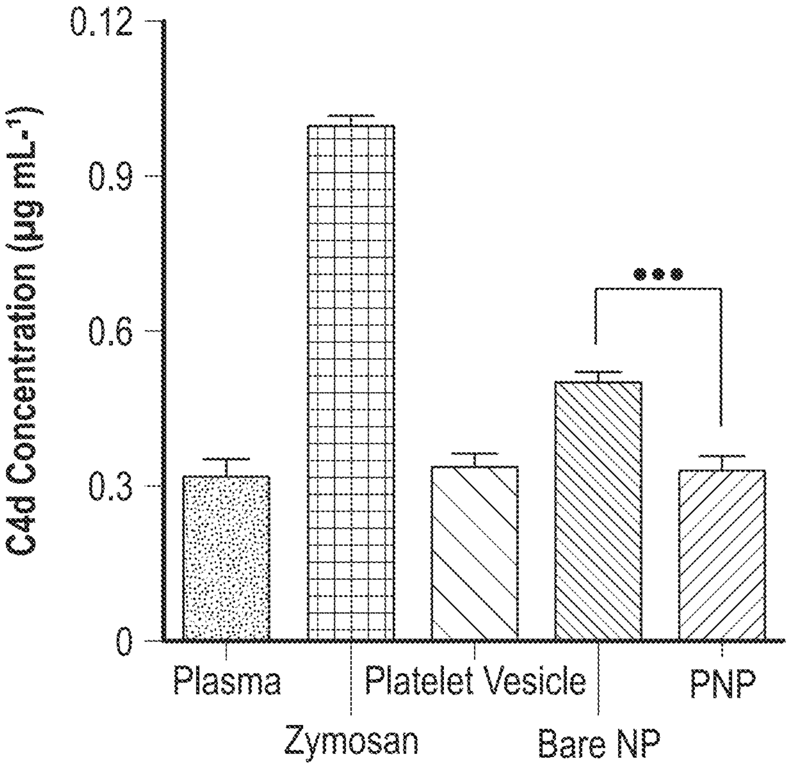
Figure 2F:
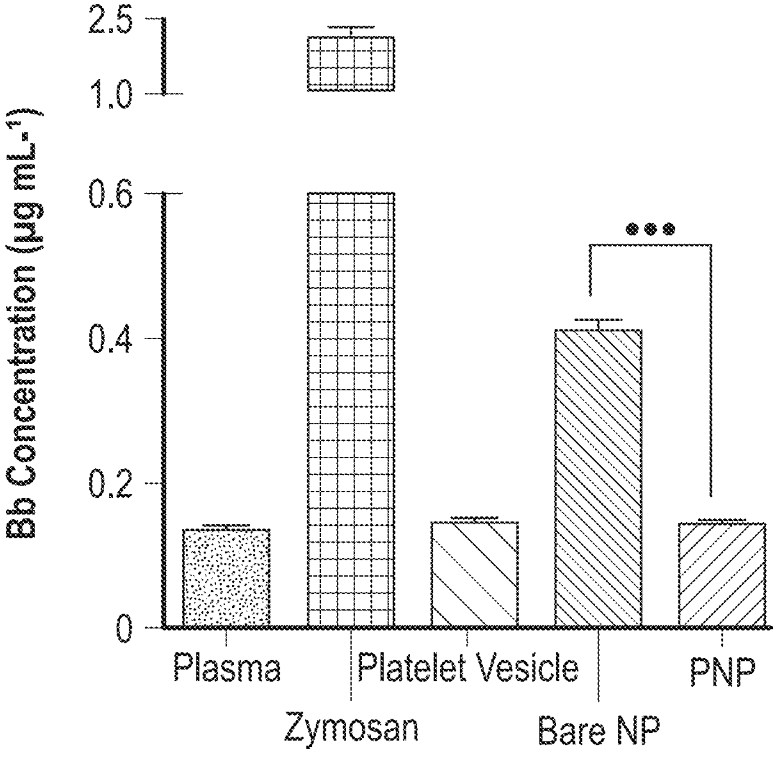

Examination of PNPs' immunocompatibility was conducted using differentiated human THP-1 macrophage-like cells. The platelet membrane cloaking reduced particle internalization in a CD47-specific manner[24], as blocking by anti-CD47 antibodies increased the cellular uptake (FIG. 2*d*). The PNPs were further investigated for their interactions with the complement system based on quantifications of C4d and Bb split products. Following incubation in human plasma, complement activation was observed with bare NPs, reflecting their susceptibility to opsonization as well as the spontaneous reaction between C3 thioesters and the hydroxyl groups on the PLGA particles[25]. In contrast, an equal amount of PNPs mixed with autologous plasma showed no observable complement activation (FIG. 2*e,f*). This suppression of the complement system can be attributed to membrane-bound complement regulator proteins such as CD55 and CD59[26] (FIG. 6). The lack of complement activation by the PNPs also attests to the completeness of the membrane cloaking, which shields the polymeric cores from plasma exposure and minimizes the risk of anaphylatoxin generation frequently associated with injectable nanocarriers[27].

Figure 3A:
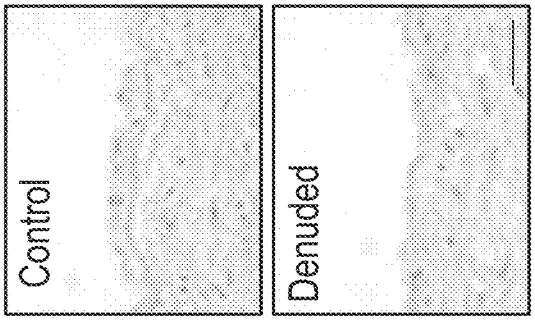
FIGS. 3A-3J show adherence to damaged human and rodent vasculatures.
Figure 3B:
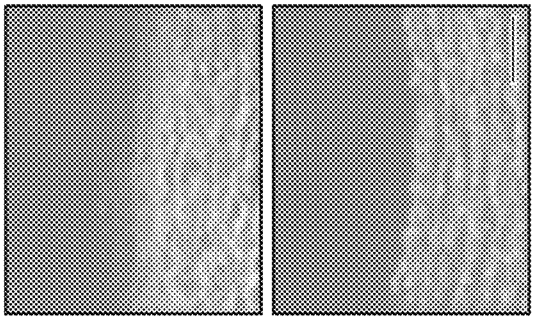
Figure 3C:
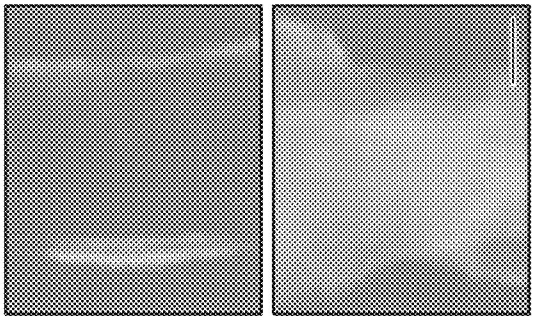
Figure 3D:
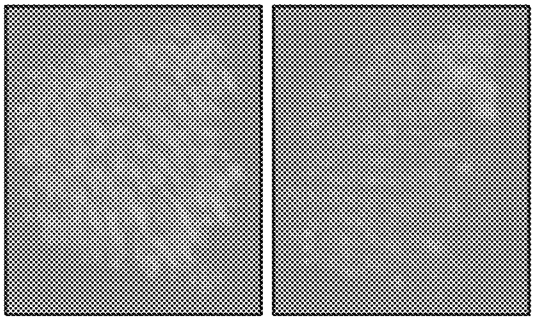
Figure 3E:
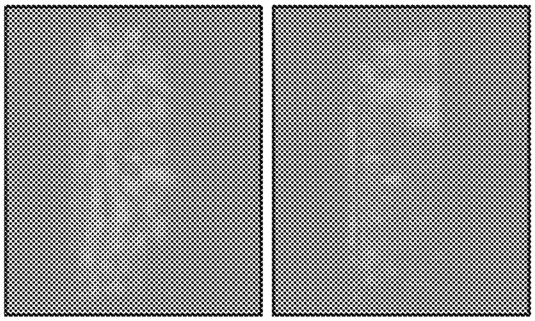
Figure 3F:
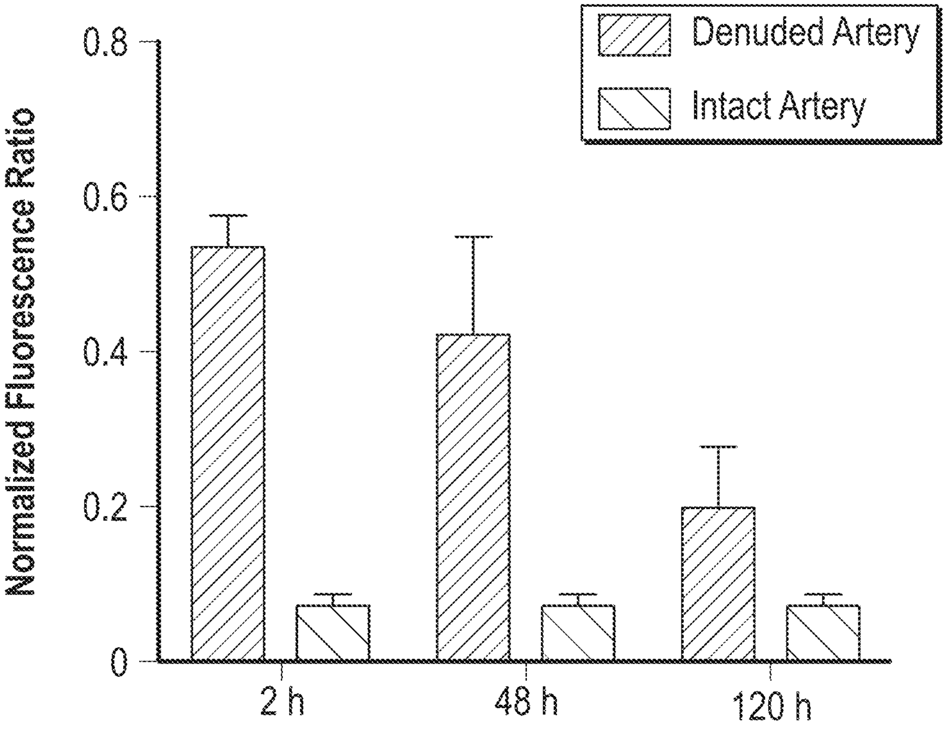
Figure 3G:
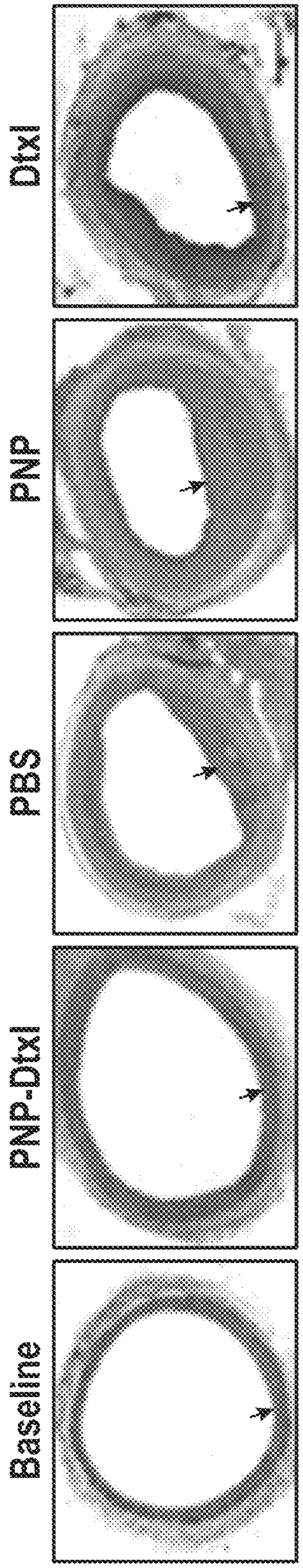
Figure 3H:
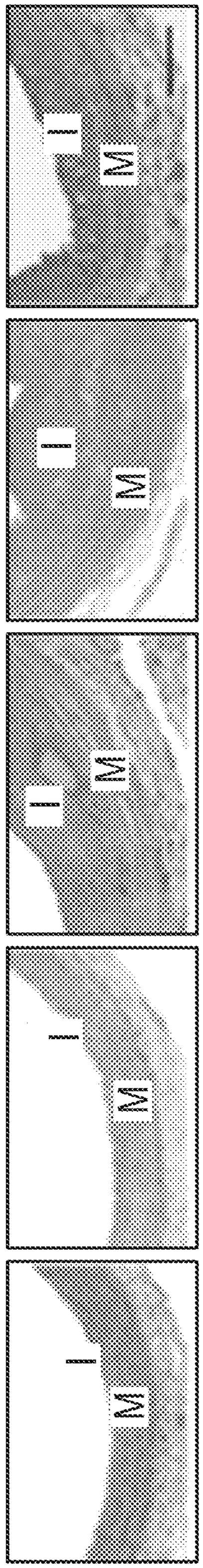
Figure 3I:
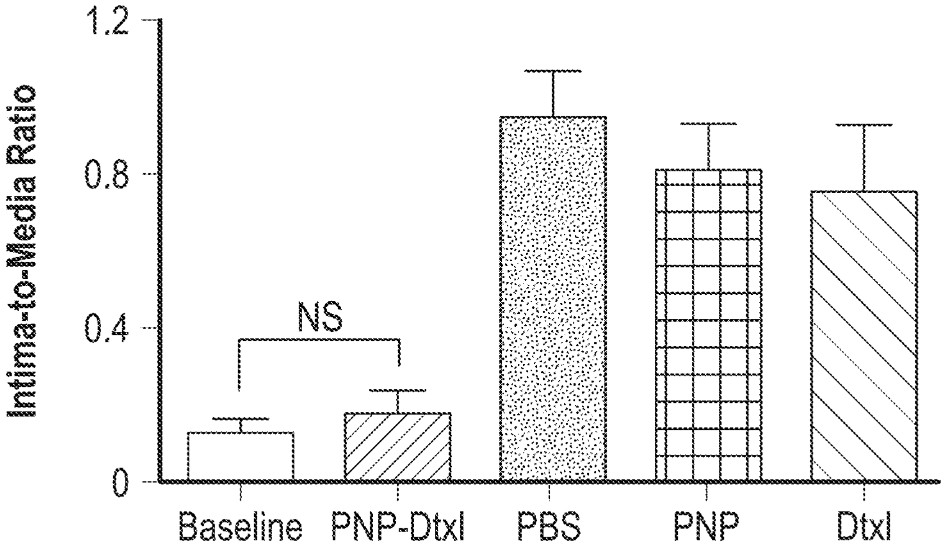
Figure 3J:
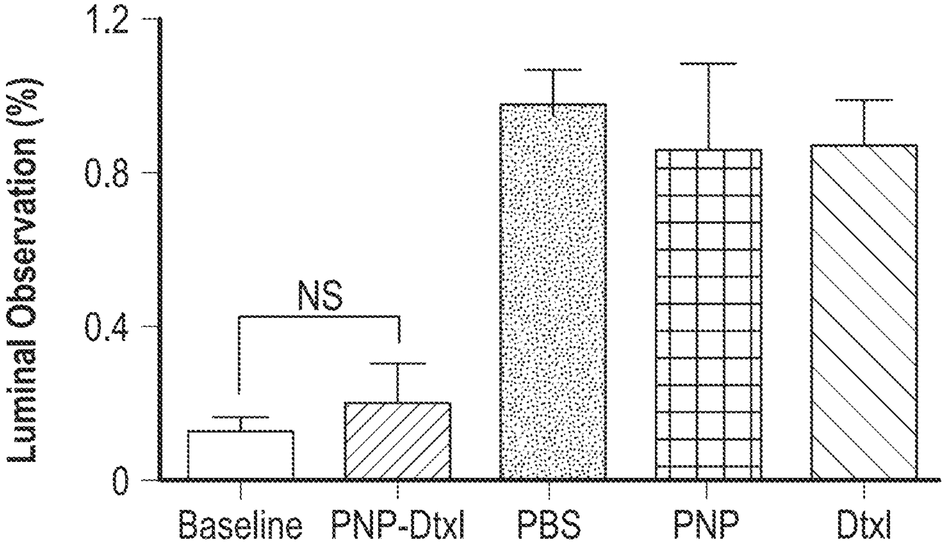
Figure 9A:
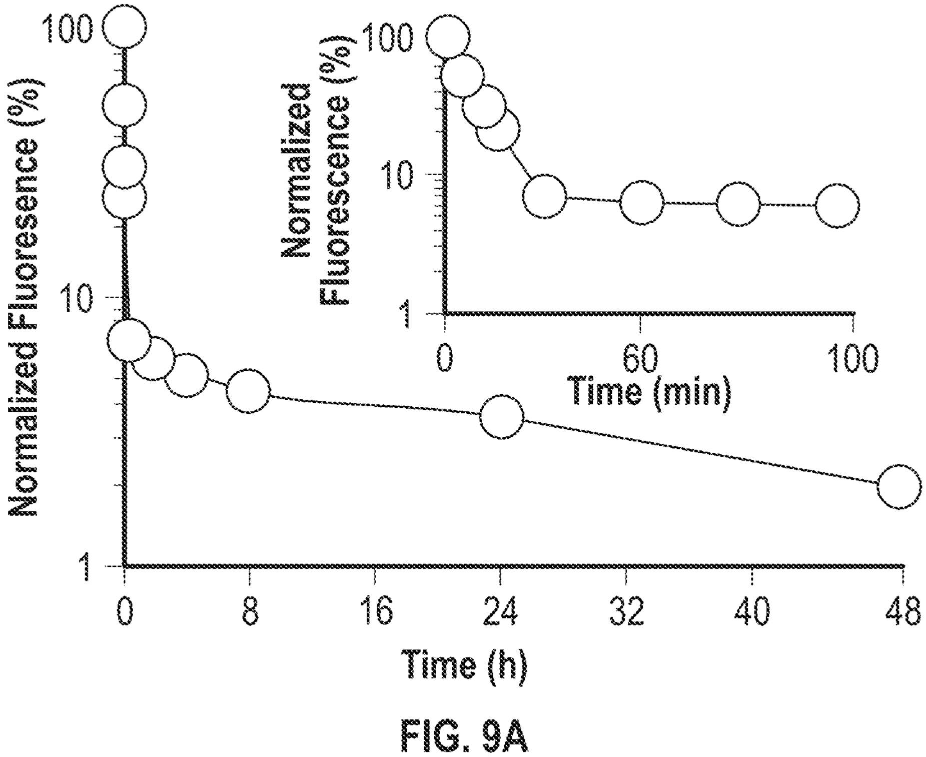
FIGS. 9A-9C show pharmacokinetics, biodistribution, and safety of PNPs.
Figure 9B:
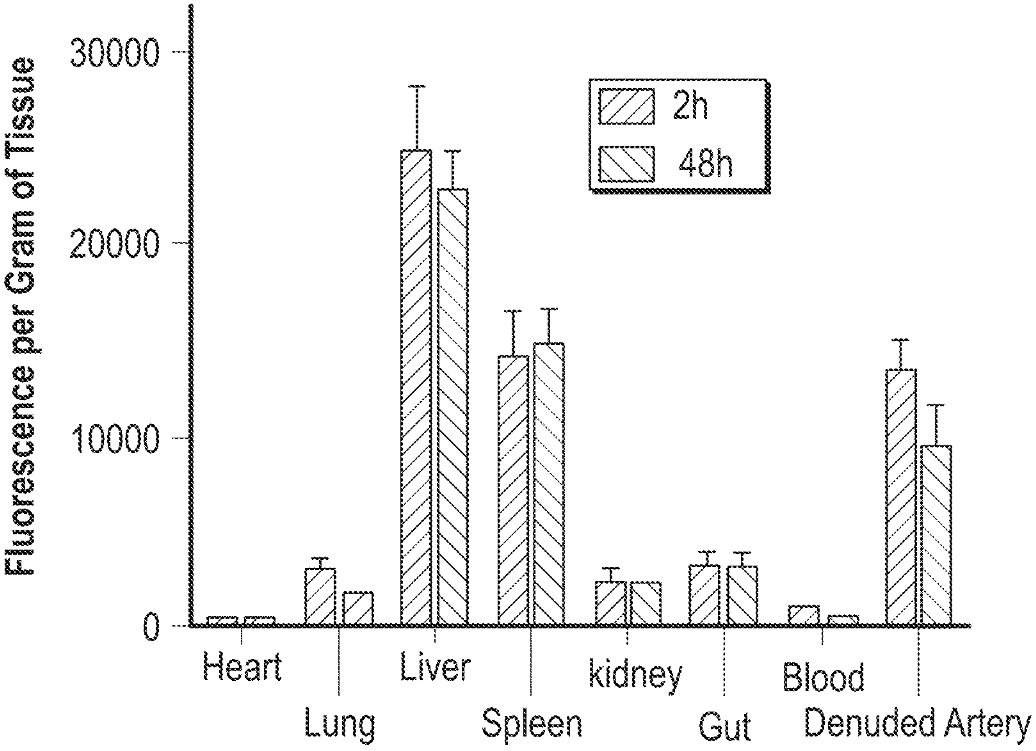
Figure 9C:
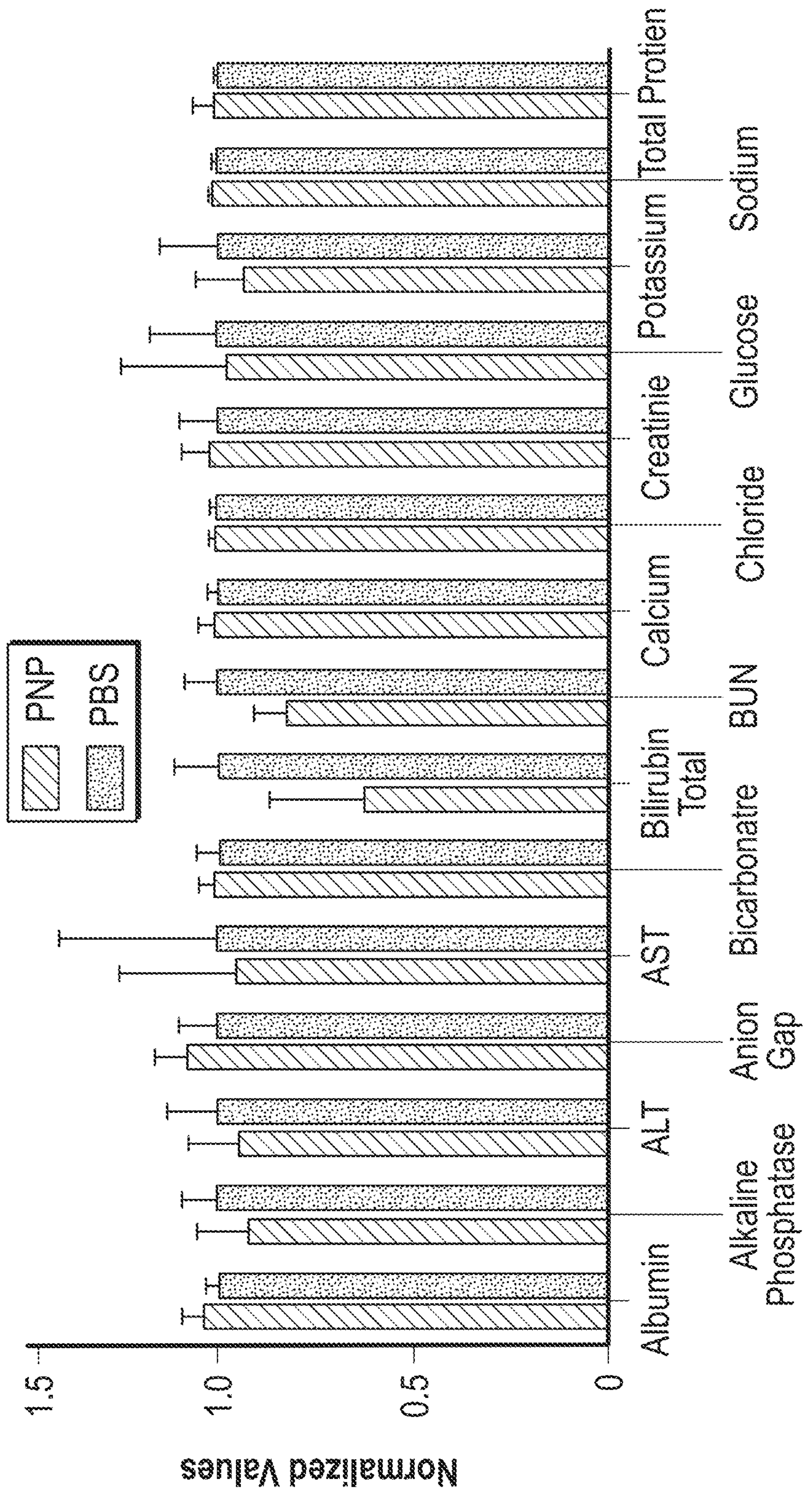
Figure 10A:
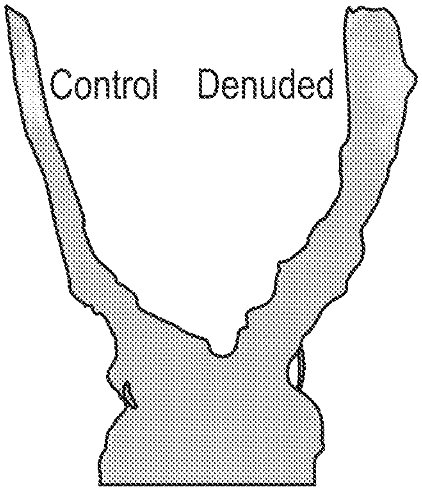
FIGS. 10A-10E show PNP targeting of damaged vasculatures upon intravenous injection to rats with angioplasty-induced arterial denudation.
Figure 10B:
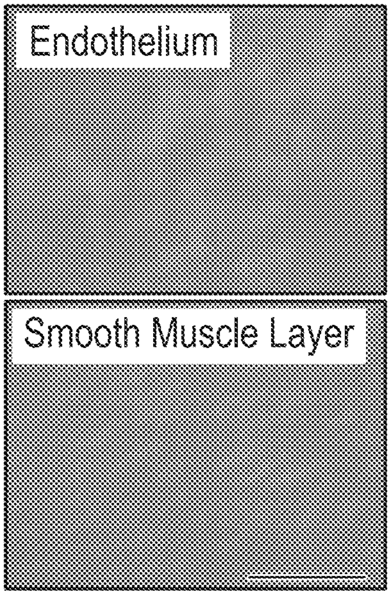
Figure 10C:
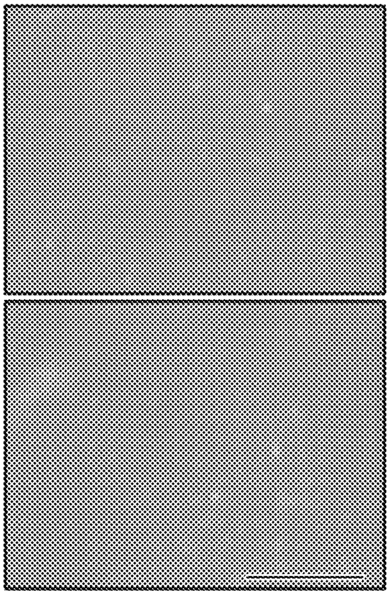
Figure 10D:
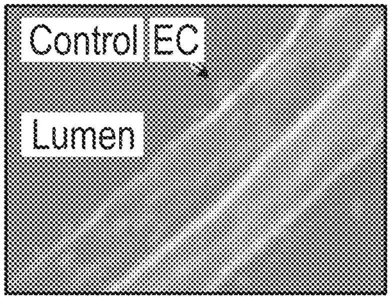
Figure 10E:
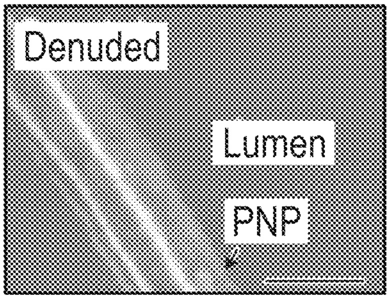
Figures 11A, 11B:
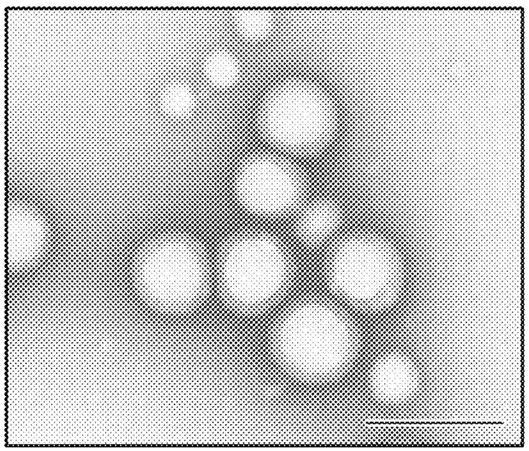
FIGS. 11A-11E show characterizations of drug-loaded cell membrane cloaked nanoparticles.
Figure 11C:
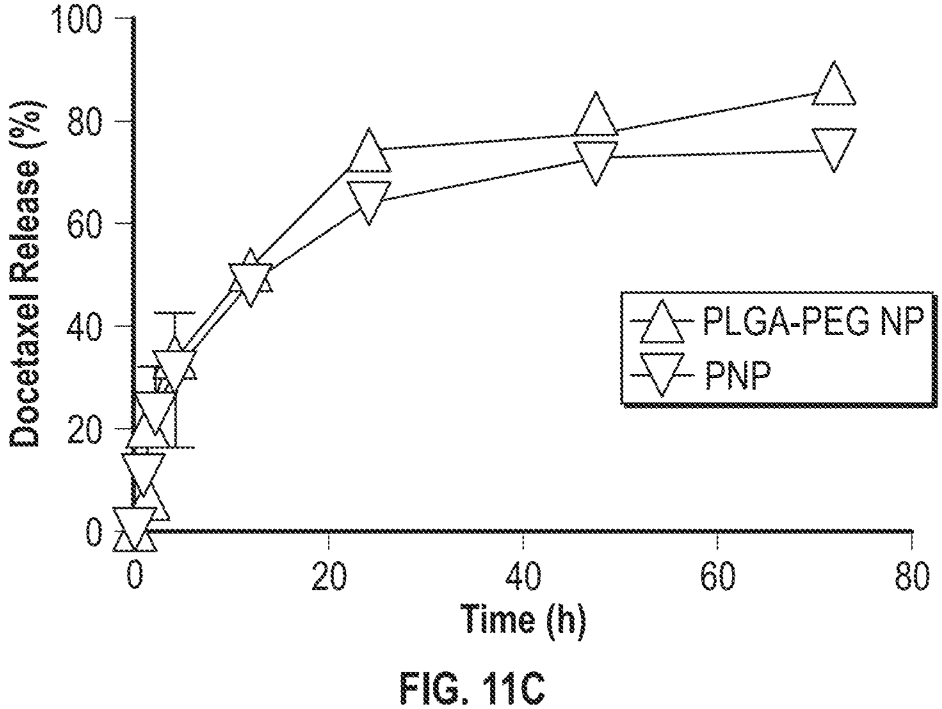
Figure 11D:
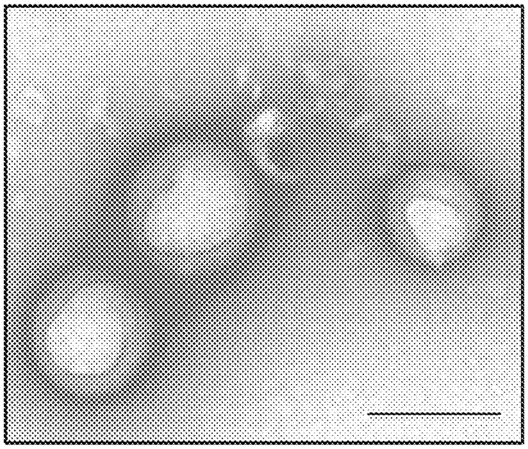
Figure 11E:
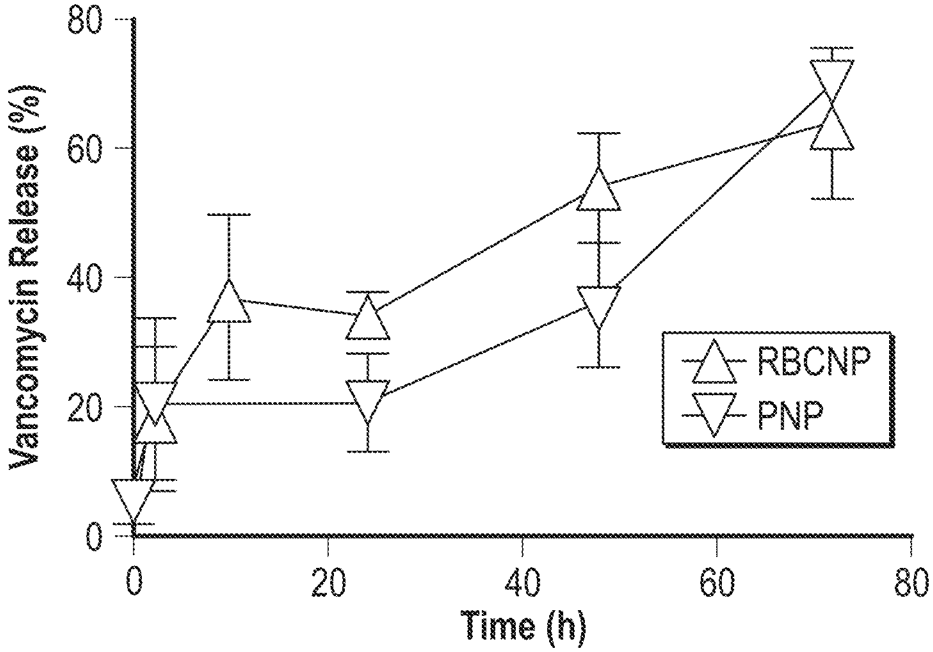
Figure 12A:
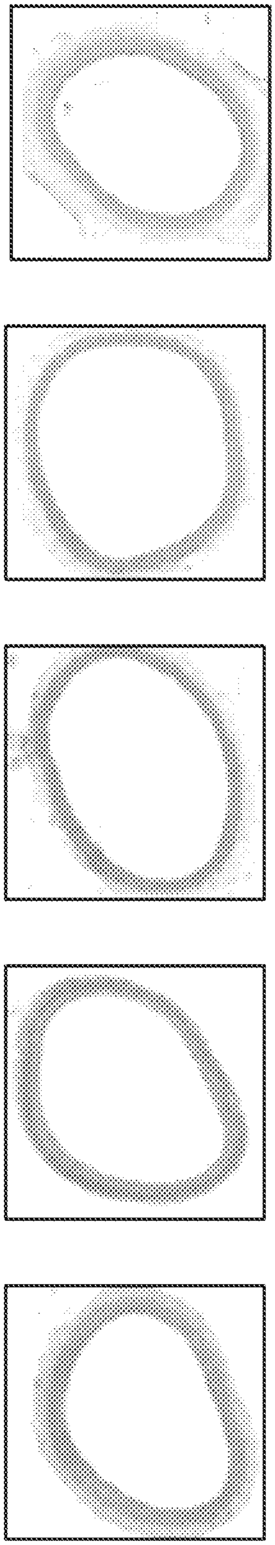
FIGS. 12A-12E show treatment of an experimental rat model of coronary restenosis. H&E-stained arterial cross-sections reveal the vascular structure of non-damaged arteries (serving as baseline) and denuded arteries following treatment with PNP-Dtxl, PBS, PNP with no docetaxel content, or free docetaxel. Scale bar=200 μm.
Figure 12B:
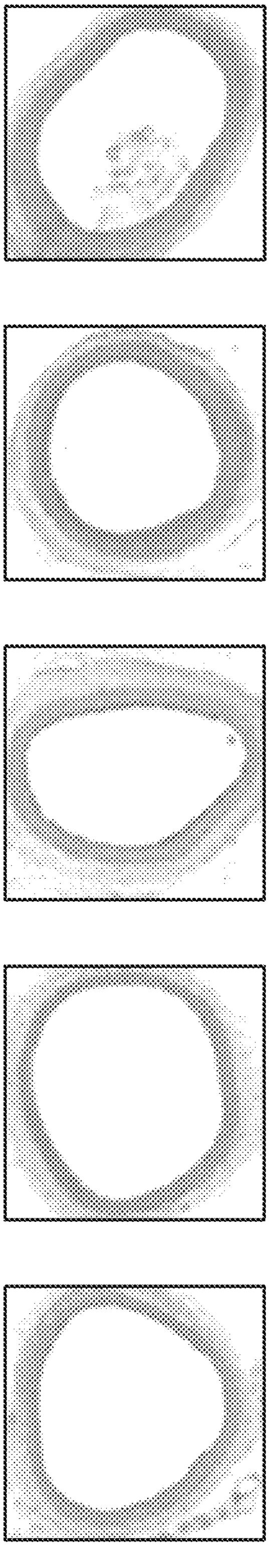
Figure 12C:
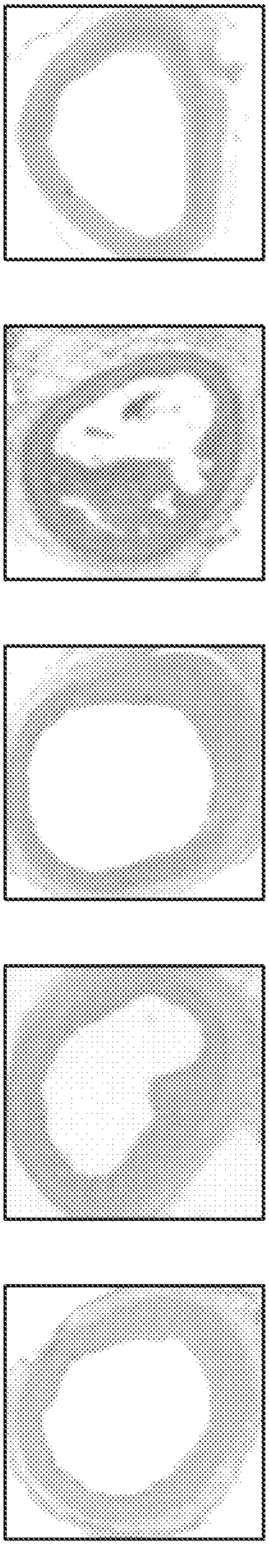
Figure 12D:
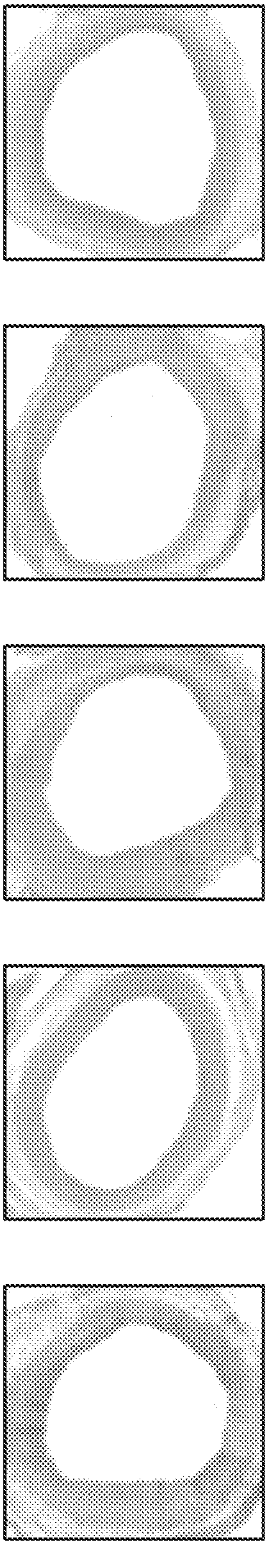
Figure 12E:
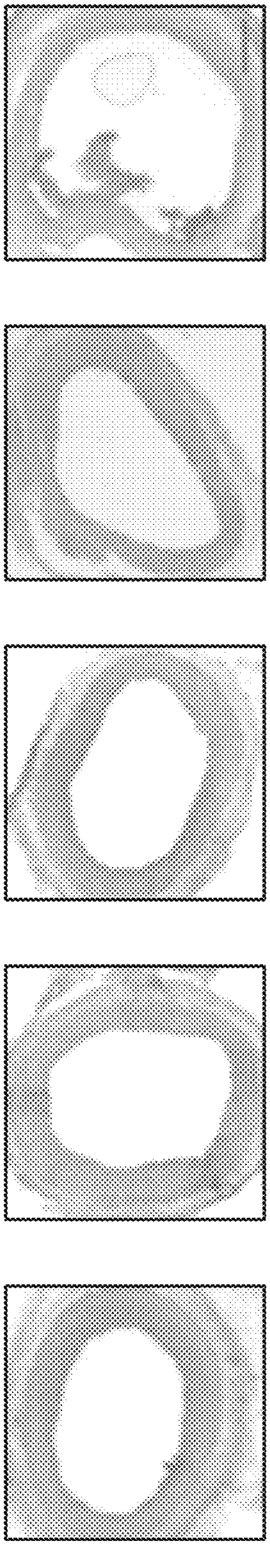

The PNP's therapeutic potential was first examined by assessing their selective adherence to damaged vasculatures. A segment of the human carotid artery was surgically scraped to expose the subendothelial matrix (FIG. 3*a*). The intact and damaged artery samples were subsequently incubated with fluorescently labeled PNPs for 30 sec followed by repeated PBS washes. The resulting arterial cross-sections and en face visualizations revealed that the denuded artery was more prone to PNP adhesion than the intact artery (FIGS. 3B, 3C). In FIG. 3C, it can also be observed that PNPs preferentially bind to the edges of the intact artery, where subendothelium was exposed upon tissue incision. This selective PNP adhesion was further validated in a rat model of angioplasty-induced arterial injury. Pharmacokinetic analyses and biodistribution studies showed that >90% of the PNPs were distributed to tissues 30 min after intravenous injection, with liver and spleen being the primary distribution organs (FIGS. 9A-9B). A comprehensive blood chemistry panel analysis revealed that the PNPs did not inflict observable adverse effects in the rats (Extended Data FIG. 6c). Selective particle binding to the denuded artery was observed upon examination of the aortic branch 2 h following PNP administration (FIG. 3D and FIGS. 10A-10E). The PNPs were localized on the luminal side above the smooth muscle layer (FIG. 3E), and retention at the injury site lasted for at least 5 days (FIG. 3F). In a rat model of coronary restenosis, therapeutic relevance of platelet-mimicking delivery was examined using docetaxel-loaded PNPs (PNP-Dtxl) (FIGS. 11A-11E). PNP-Dtxl treatment on day 0 and 5 at 0.3 mg $kg^{-1}$ of docetaxel dosing potently inhibited neointima growth in balloon-denuded rats as evidenced by the arterial cross-sections collected on day 14 (FIGS. 3G, 3H and FIGS. 12A-12E). To quantitatively evaluate the vascular remodeling, intima-to-media ratio (I/M) and luminal obliteration were calculated. As compared to free docetaxel, which resulted in an I/M of 0.76±0.18 and a luminal obliteration of 33.6%, PNP-Dtxl yielded significantly lower values of 0.181±0.06 and 8.0%, respectively (P≤0.000) (FIG. 3*i-j*). These results demonstrate the benefit of PNP-directed delivery in improving drug localization to diseased vasculatures.

The vast medical relevance of platelets has inspired many platelet-mimicking systems that target dysfunctional vasculature in cardiovascular diseases[8,9], traumas[10,11,13], cancers[12], and acute inflammations[29]. The present PNP platform exploits platelet membrane in its entirety to enable biomimetic interactions with proteins, cells, tissues, and microorganisms. Toward translation, the platform would benefit from existing infrastructures and logistics for transfusion medicine, polymeric nanotherapeutics, and cell-derived pharmaceutics. Prior works on the cell membrane cloaking approach demonstrated high cloaking efficiency[30] and viable storage[18] upon platform optimization (FIGS. 5F-5H). By employing large-scale purification and dispersion techniques commonly applied to biologics, reliable platelet membrane derivation and PNP production can be envisioned.

Method Summary

Platelets were collected from human whole blood via centrifugal separation, and membrane vesicles were derived from the cells through a combination of freeze-thaw cycles, washing, and sonication. PNPs were prepared by fusing platelet vesicles onto preformed PLGA nanoparticles via ultrasonic dispersion. Drug-loaded PNPs were prepared by cloaking drug-loaded nanoparticle cores with platelet membranes. Size and surface zeta potential of PNPs were obtained from DLS measurements. Core-shell structure of PNPs was examined by TEM. PNPs were characterized for protein retention using SDS-PAGE, and specific immunomodulatory and adhesion membrane proteins were subsequently identified using western blotting. Membrane sidedness was examined based on the orientation of CD47 transmembrane proteins on the PNPs.

Differential binding of PNPs to subendothelium was assessed based on particle retention on human type IV collagen-coated plates seeded with HUVECs and to subendothelial matrices of decellularized human umbilical cord arteries. Immunocompatibility of PNPs was assessed through uptake by differentiated THP-1 cells and through both classical and alternative complement activation. Adherence to damaged vasculatures was examined through an ex vivo study with denuded human carotid arteries and an in vivo study with rats following angioplasty-induced endothelial denudation. Therapeutic efficacy of docetaxel-loaded PNPs was assessed in an experimental rat model of coronary restenosis.

Methods

Human platelet isolation and platelet membrane derivation: Fresh type $O^-$ human blood with EDTA as an anticoagulant was purchased from BioreclamationIVT. To isolate platelets from whole blood, the blood sample was first centrifuged at 100×g for 20 min at room temperature to separate red blood cells and white blood cells from platelet rich plasma (PRP). The PRP was then centrifuged at 100×g for 20 min to remove remaining blood cells. PBS buffer containing 1 mM of EDTA and 2 μM of prostaglandin E1 (PGE1, Sigma Aldrich) was added to the purified PRP to prevent platelet activation. Platelets were then pelleted by centrifugation at 800×g for 20 min at room temperature, following which the supernatant was discarded and the platelets were resuspended in PBS mixed with protease inhibitor tablets (Pierce). 1.5 mL aliquots of platelet solution containing ~$3\times10^9$ platelets were used to cloak 1 mg of PLGA nanoparticles.

Platelet membrane was derived by a repeated freeze-thaw process. Aliquots of platelet suspensions were first frozen at −80° C., thawed at room temperature, and pelleted by centrifugation at 4000×g for 3 min. Following three repeated washes with PBS solution mixed with protease inhibitor tablets, the pelleted platelet membranes were suspended in water and sonicated in a capped glass vial for 5 min using a Fisher Scientific FS30D bath sonicator at a frequency of 42 kHz and a power of 100 W. The presence of platelet membrane vesicles was verified by size measurement using dynamic light scattering (DLS) and morphological examination by transmission electron microscopy (TEM).

Platelet membrane-cloaked nanoparticle (PNP) preparation and characterization: 100 nm polymeric cores were prepared using 0.67 dL $g^{-1}$ carboxyl-terminated 50:50 poly (lactic-co-glycolic) acid (PLGA) (LACTEL Absorbable Polymers) in a nanoprecipitation process. 1 mL of 10 mg $mL^{-1}$ PLGA solution in acetone was added dropwise to 3 mL of water. For fluorescently labeled nanoformulations, 1,1'-dioctadecyl-3,3,3',3'-tetramethylindodicarbocyanine perchlorate (DiD, ex=644 nm/em=665 nm, Life Technologies) was loaded into the polymeric cores at 0.1 wt %, The mixture was then stirred in open air for 1 h and placed in vacuum for another 3 h. The resulting nanoparticle solution was filtered with 10 kDa MWCO Amicon Ultra-4 Centrifugal Filters (Millipore). Platelet membrane cloaking was then accomplished by dispersing and fusing platelet membrane vesicles with PLGA particles via sonication using an FS30D bath sonicator at a frequency of 42 kHz and a power of 100 W for 2 min. The size and the surface zeta potential of the resulting PNPs were obtained by DLS measurements using a Malvern ZEN 3600 Zetasizer. PBS stability was examined by mixing 1 mg $mL^{-1}$ of PNPs in water with 2×PBS at a 1:1 volume ratio. Storability of PNPs was examined by suspending PNPs in 10% sucrose. The nanoparticle solutions were subject to either a freeze-thaw cycle or lyophilization followed by resuspension. The resulting particle solution was then monitored for particle size using DLS. The structure of PNPs was examined with TEM following negative staining with 1 wt % uranyl acetate using an FEI 200 kV Sphera microscope. RBCNPs were prepared using the same polymeric cores and RBC membranes of equivalent total surface area to the platelet membranes using a previously described protocol[16]. The RBCNPs were characterized using DLS and had similar size and zeta potential as the PNPs.

Docetaxel-loaded PLGA nanoparticle cores were prepared via a nanoprecipitation process. 10 wt % docetaxel was added to 5 mg PLGA in acetone and precipitated dropwise into 3 mL water. The solvent was evaporated as described above and free docetaxel was removed via repeated wash steps. Vancomycin-loaded nanoparticles were synthesized using a double emulsion process. The inner aqueous phase consisted of 25 μL of vancomycin (Sigma Aldrich) dissolved in 1 M NaOH at 200 mg $mL^{-1}$. The outer phase consisted of 500 IL of PLGA polymer dissolved in dichloromethane at 50 mg $mL^{-1}$. The first emulsion was formed via sonication at 70% power pulsed (2 sec on/1 sec off) for 2 min on a Fisher Scientific 150E Sonic Dismembrator. The resulting emulsion was then emulsified in aqueous solution under the same dispersion setting. The final w/o/w emulsion was added to 10 mL of water and the solvent was evaporated in a fume food under gentle stirring for 3 h. The particles were collected via centrifugation at 80,000×g in a Beckman Coulter Optima L-90K Ultracentrifuge. The particles were washed and resuspended in water. Upon preparation of drug-loaded PLGA cores, cell membrane coating was performed by adding the appropriate surface area equivalent of either platelet or RBC membrane followed by 3 min of sonication in a Fisher Scientific FS30D Bath Sonicator. Particle size, polydispersity (PDI), and surface zeta potential were characterized using DLS. Drug loading yield and release rate were quantified by high performance liquid chromatography (HPLC). Drug release was determined by dialyzing 500 μL of particle solution at a concentration of 2.67 mg $mL^{-1}$ in PBS using 3.5K MWCO Slide-A-Lyzers (Thermo Scientific).

Examination of platelet membrane proteins: PNPs were purified from unbound proteins or membrane fragments via centrifugation at 16,000×g in 10% sucrose. Platelet-rich plasma, platelets, platelet membrane vesicles, and PNPs were then normalized to equivalent overall protein concentration using a Pierce BCA Protein Assay Kit (Life Technologies). The samples containing equivalent total proteins were then lyophilized, prepared in lithium dodecyl sulfate (LDS) sample loading buffer (Invitrogen), and separated on a 4-12% Bis-Tris 10-well minigel in MOPS running buffer using a Novex Xcell SureLock Electrophoresis System (Life Technologies). For membrane protein visualization, the gel was stained using SimplyBlue SafeStain solution (Life Technologies) following the manufacturer's instructions and imaged using a gel imager. Identification of key membrane proteins via western blotting was performed using primary antibodies including mouse anti-human CD47 (Biolegend, CC2C6), mouse anti-human CD55 (Biolegend, JS11), mouse anti-human CD59 (Biolegend, H19), mouse anti-human integrin αIIbβ3 (Biolegend, PAC-1), mouse anti-human integrin α2 subunit (Abgent, AP17907b-ev), mouse anti-human integrin α5 subunit (Biolegend, NKI-SAM-1), mouse anti-human integrin α6 subunit (Biolegend, GoH3), mouse anti-human integrin β1 subunit (Biolegend, TS2/16), mouse anti-human GPIbα (Biolegend, HIP1), mouse anti-human GPIV (Biolegend, 5-271), rabbit anti-human GPV (Santa Cruz Biotech, H-300), rabbit anti-human GPVI (Santa Cruz Biotech, H-5), rabbit anti-human GPIX (Santa Cruz Biotech, A-9), and mouse anti-human CLEC-2 (Santa Cruz Biotech, 53Ex9). A goat anti-mouse IgG-HRP conjugate (Biolegend, Poly4053) and a donkey anti-rabbit IgG-HRP conjugate (Biolegend, Poly4064) were used for secondary staining based on the isotype of the primary antibodies. The nitrocellulose membrane was then incubated with ECL western blotting substrate (Pierce) and developed with the Mini-Medical/90 Developer (ImageWorks).

Examination of protein sidedness on PNPs: For immunogold staining, a drop of the PNP solution (1 mg $mL^{-1}$) was deposited onto a glow-discharged carbon-coated grid. The grid was then washed 3 times with PBS, blocked with 1% BSA for 15 min, and stained with 0.5 mg $mL^{-1}$ of anti-CD47 targeted to either the intracellular or extracellular domain of the protein. Following 1 h of incubation, the samples were rinsed with PBS containing 1% BSA for 6 times and stained with anti-rabbit IgG gold conjugate (5 nm) solution (Sigma Aldrich) for another hour. Following 6 times of PBS washing, the samples were fixed with 1% glutaraldehyde in PBS for 5 min and washed with water for 6 times. The sample grids were subsequently stained with 2% vanadium solution (Abcam) and visualized using an FEI 200 kV Sphera microscope.

For flow cytometric analysis, 2.0 μm carboxyl-functionalized polystyrene beads at a concentration of 4 wt % (Life Technologies) were functionalized with rabbit N-terminus-targeted (extracellular) anti-human CD47 (Aviva Biosystems, ARP63284), rabbit intracellular-domain-targeted anti-CD47 (Genetex, EPR4150(2)), or rabbit anti-ovalbumin (Abcam, ab1221) as a sham antibody via EDC/NHS chemistry. The resulting antibody-modified beads were re-suspended in 100 μL of DI water. The bead solution was first incubated with 1 mg of bovine serum albumin (BSA, Sigma Aldrich) to block non-specific interactions and then mixed with 1 mL of fluorescently labeled PNPs (200 μg $mL^{-1}$). The mixture solution was incubated at room temperature for 2 h and then centrifuged to remove the unbound PNPs. The collected polystyrene beads were then subjected to flow cytometric analysis.

Platelet aggregation assay: Platelets, platelet membrane vesicles, and PNPs of equivalent membrane content were prepared and examined for platelet-activating molecules, including thrombin, ADP, and thromboxane, using a SensoLyte 520 Thrombin Activity Assay Kit (AnaSpec), ADP Colorimetric/Fluorometric Assay Kit (Sigma Aldrich), and Thromboxane B2 ($TXB_2$) ELISA Kit (Enzo Life Sciences), respectively, based on the manufacturers' instructions.

Aggregation of platelets in the presence of PNPs was assessed using a spectrophotometric method. 1 mL aliquot of platelet rich plasma (PRP) was first prepared from human whole blood with sodium citrate as the anti-coagulant. The plasma was then loaded into a cuvette followed by addition of 500 μL of 2 mg $mL^{-1}$ PNPs in PBS solution. As negative and positive controls, the PRP was mixed with 500 μL of PBS or 500 μL of PBS containing 0.5 IU $mL^{-1}$ of human thrombin (Sigma Aldrich), respectively. The cuvettes were immediately placed in a TeCan Infinite M200 reader and monitored for change in absorbance at 650 nm over time, and platelet aggregation was observed based on the reduction of turbidity.

Collagen binding study: Collagen type IV derived from human placenta (Sigma Aldrich) was reconstituted to a concentration of 2.0 mg $mL^{-1}$ in 0.25% acetic acid. 200 μL of the collagen solution was then added to a 96-well assay plate and incubated overnight at 4° C. Prior to the collagen binding study, the plate was blocked with 2% BSA and washed three times with PBS. For the collagen binding study, 100 μL of 1 mg $mL^{-1}$ DiD-loaded nanoformulations in water were added to the collagen-coated and non-collagen-coated plates. Following 30 sec of incubation, the plates were washed three times. Retained nanoparticles were then dissolved with 100 μL of DMSO for fluorescence quantification using a TeCan Infinite M200 reader.

Differential adhesion to endothelial and collagen surfaces: Collagen type IV was coated on 8-well Lab-Tek 11 chamber slides (Nunclon) as described above. The collagen-coated chamber slides were used to seed HUVECs (American Type Culture Collection) and cultured in HUVEC Culture Medium (Sigma Aldrich) supplemented with 10% fetal bovine serum for 24 h. The cells were then incubated with 1 mg $mL^{-1}$ DiD-loaded PNPs in PBS at 4° C. for 30 sec. Next the cells were washed with PBS three times and fixed with tissue fixative (Millipore) for 30 min at room temperature. Fluorescence staining was done with 4'6-diamidino-2-phenylinodle (DAPI, Life Technologies) for the nuclei and 22-(n-(7-nitrobenz-2-oxa-1,3-diazol-4-yl)amino)-23,24-bisnor-5-cholen-3β-ol (NBD cholesterol, Life Technologies) for the cytosol before mounting the cells in ProLong Gold antifade reagent (Life Technologies) and imaged using a DeltaVision deconvolution scanning fluorescence microscope. Z-stacks were collected at 0.25 μm intervals over 10 μm. The images were deconvolved and superimposed. DiD fluorescence signal over collagen and endothelial surfaces as defined by the boundaries of NBD fluorescence were analyzed using ImageJ. PNP retention over collagen and endothelial surfaces was quantified based on 10 distinct images in which the average fluorescence per unit area was analyzed.

Cellular uptake study with macrophage-like cells: THP-1 cells (American Type Culture Collection) were maintained in RPMI 1640 media (Life Technologies) supplemented with 10% FBS (Sigma Aldrich). THP-1 cells were differentiated in 100 ng $mL^{-1}$ phorbol myristate acetate (PMA, Sigma Aldrich) for 48 h and differentiation was visually confirmed by cellular attachment to petri dishes. For the cellular uptake study, the differentiated macrophage-like cells were incubated with DiD-loaded PNPs, anti-CD47 blocked PNPs, and bare NPs at 100 μg $mL^{-1}$ in culture media. Following 30 min of incubation at 37° C. the macrophage-like cells were scraped off the petri dish and washed three times in PBS to remove non-internalized particles. Flow cytometry was performed to examine nanoparticle uptake by the macrophage-like cells. All flow cytometry studies were conducted on a FACSCanto II flow cytometer (BD Biosciences) and the data was analyzed using FlowJo software from Tree Star. The mean fluorescence was plotted in a bar chart with error bars representing the standard error. Statistical analysis was performed based on a two-tailed, unpaired t-test.

Complement activation study: To assess complement system activation, two complement split products (C4d and Bb) were analyzed using enzyme-linked immunosorbent assay kits (Quidel Corporation). The nanoparticles were incubated with human serum at a volume ratio of 1:5 in a shaking incubator (80 rpm) at 37° C. for 1 h. The reaction was then stopped by adding 60 volumes of PBS containing 0.05% Tween-20 and 0.035% ProClin 300. Complement system activation of the nanoparticles was assayed following the manufacturer's instructions, and zymosan was used as a positive control.

PNP adherence to human carotid artery: Human umbilical cord was collected under the approval of the Institutional Review Board (IRB) at the University of California. San Diego. and human carotid arteries were collected under the approval of the IRB at the University of Southern California. To derive decellularized arterial extracellular matrix (ECM), human arteries were carefully dissected from the umbilical cord and removed from the surrounding Wharton's jelly, and subsequently incubated in 2% sodium dodecyl sulfate (SDS, Sigma Aldrich) for 72 h. The decellularized tissue was then rinsed with PBS and incubated in PBS solution containing 200 μg $mL^{-1}$ PNPs for 30 sec. The sample was then transferred to PBS solution and rinsed extensively prior to examination by scanning electron microscopy (SEM). A control decellularized arterial tissue sample without PNP incubation was prepared and visualized for comparison.

To examine PNP binding on denuded vascular walls, approximately 2 mm thick fresh human carotid artery sections were dissected and placed in normal saline on ice and transported immediately to the laboratory for a PNP binding study. To create the vascular characteristics of damaged arteries, an excised artery sample was surgically scraped on its luminal side with forceps to remove the endothelial layer. Successful denudation was confirmed via microscopy visualization. Prior to the nanoparticle binding experiment, both damaged and non-damaged artery samples were rinsed with PBS solution. The PNP binding experiment was performed by incubating the arterial samples in PBS solution containing 200 μg $mL^{-1}$ of DiD-loaded PNPs for 30 sec. The samples were then transferred to PBS solution and rinsed extensively prior to visualization by fluorescence microscopy. Endogenous tissue components such as collagen and elastin were identified based on their autofluorescence, which excites and emits maximally at 300-500 nm and was captured using a FITC filter. DiD fluorescence was captured using a Cy5 filter to examine the deposition of PNPs. The arterial samples were imaged via a cross-sectional view of a histological section and a top-down view on the luminal side. The images were normalized to a reference illumination image for proper comparison.

Pharmacokinetics, biodistribution and safety of PNPs in a rat model of angioplasty-induced arterial denudation: All animal experiments were performed in accordance with NIH guidelines and approved by the Animal Care Committee of the University of California, San Diego. For the pharmacokinetics study, adult male Sprague-Dawley rats weighing 300-350 g (Harlan Laboratories) were administered with DiD-labeled PNPs and their blood was collected at specific time points via tail-vein blood sampling for fluorescence quantification. For the safety study, rats were injected with 1 mL of 5 mg $mL^{-1}$ of PNPs on day 0 and day 5 followed by blood collection on day 10 for comprehensive metabolic panel analysis. Rats receiving equivalent PBS injections were prepared as a control.

For the biodistribution and vasculature-targeting studies, adult male Sprague-Dawley rats weighing 300-350 g (Harlan Laboratories) were subjected to carotid balloon injury. In brief, the animals were anesthetized with intraperitoneal ketamine (Pfizer) at 100 mg $kg^{-1}$ and xylazine (Lloyd Laboratories) at 10 mg $kg^{-1}$. A ventral mid-line incision (~2 cm) was made in the neck, and the left common carotid artery and carotid bifurcation was exposed by blunt dissection. Proximal of left carotid artery, inner carotid artery and external carotid artery were temporarily clamped to avoid excessive blood loss during the induction of the 2F Fogarty arterial embolectomy catheter (Edwards Lifesciences). The catheter was introduced into left carotid artery through an arteriotomy on the external carotid artery. The catheter was slowly inflated to a determined volume (0.02 mL) and withdrawn with rotation for 3 times to denude endothelium. The wound was later closed with 4-0 sutures.

Following the wound closure, rats were injected intravenously with 1 mL of 5 mg $mL^{-1}$ DiD-loaded PNPs in 10% sucrose. At specified time points following the injection, animals were euthanized by $CO_2$ inhalation. After perfusion with PBS, organs including heart, lung, liver, spleen, kidney, gut, blood, and aortic branch including both the left and right carotid arteries were carefully collected and homogenized for biodistribution analysis. The overall PNP distribution at the aortic branch was visualized using Keyence BZ-X700 fluorescence microscope. To examine the local distribution of PNP, damaged and undamaged arteries were cut longitudinally and stained with DAPI solution. En face examination was done on the luminal surfaces of denuded and intact area for the binding of PNPs. Sequences of images along z-axis (0.5 μm per section) from the intima to media layers of the carotid arteries were acquired with and Olympus ix81 fluorescence microscope. The 3D reconstruction of arterial wall from multisectional images was performed using Image J. To analyze the PNP retention, damaged and undamaged arteries collected at specified time points were homogenized, and their respective fluorescence was normalized to the liver fluorescence for comparison.

Treatment of experimental coronary restenosis: Sprague-Dawley rats following angioplasty-induced arterial denudation were injected intravenously with 1 mL of 5 mg $mL^{-1}$ docetaxel-loaded PNPs in 10% sucrose at a docetaxel dose of 0.3 mg $kg^{-1}$ on day 0 and day 5. As controls, animals receiving PBS, free docetaxel, and empty PNPs were prepared. On day 14, animals were euthanized with an overdose of ketamine-xylazine cocktail and perfused with PBS and 4% paraformaldehyde (PFA) at a pressure of 120-140 mm Hg. Segments of left and right carotid arteries were carefully dissected out, and the PFA-fixed carotid arteries were embedded with Tissue-Tek OCT compound (VWR International) in a tissue base mold and slowly submerged into pre-chilled 2-methyl butane until frozen completely. The frozen tissue block was then immediately stored at −80° C. until sectioning. Serial sectioning (15 μm per section) was performed with a Cyrotome cryostat machine (Leica), and the tissue sections were placed on polylysine-treated glass slides. Tissue sections on slides were dried at room temperature for 30 min before staining. For immunohistochemistry, frozen sections on slides were first washed with PBS to remove residual OCT medium and then subjected to standard hematoxylin and eosin (H&E) staining. Areas of intima and media were analyzed using Image J. Luminal obliteration is defined as the intima area/the area within the internal elastic lamina. Statistical analysis was performed using one-way ANOVA.

REFERENCES

1. Pelaz, B. et al. Interfacing engineered nanoparticles with biological systems: anticipating adverse nanobio interactions. *Small* 9, 1573-1584, (2013).
2. Salvati, A. et al. Transferrin-functionalized nanoparticles lose their targeting capabilities when a biomolecule corona adsorbs on the surface. *Nature Nanotech.* 8, 137-143, (2013).
3. Tenzer, S. et al. Rapid formation of plasma protein corona critically affects nanoparticle pathophysiology. *Nature Nanotech.* 8, 772-781, (2013).
4. Born, G. V. & Cross, M. J. The aggregation of blood platelets. *J. Physiol.* 168, 178-195, (1963).
5. Kieffer, N. & Phillips, D. R. Platelet membrane-glycoproteins—functions in cellular interactions. *Annu. Rev. Cell Biol.* 6, 329-357, (1990).
6. Fitzgerald, J. R., Foster, T. J. & Cox, D. The interaction of bacterial pathogens with platelets. *Nat. Rev. Microbiol.* 4, 445-457, (2006).
7. Yeaman, M. R. Platelets in defense against bacterial pathogens. *Cell. Mol. Life. Sci.* 67, 525-544, (2010).
8. Peters, D. et al. Targeting atherosclerosis by using modular, multifunctional micelles. *Proc. Natl. Acad. Sci. U.S.A.* 106, 9815-9819, (2009).
9. Chan, J. M. et al. Spatiotemporal controlled delivery of nanoparticles to injured vasculature. *Proc. Natl. Acad. Sci. U.S.A.* 107, 2213-2218, (2010).
10. Bertram, J. P. et al. Intravenous hemostat: nanotechnology to halt Bleeding. *Sci. Trans. Med.* 1, 11ra22, (2009).
11. Modery-Pawlowski, C. L. et al. Approaches to synthetic platelet analogs. *Biomaterials* 34, 526-541, (2013).
12. Simberg, D. et al. Biomimetic amplification of nanoparticle homing to tumors. *Proc. Natl. Acad. Sci. U.S.A.* 104, 932-936, (2007).
13. Anselmo, A. C. et al. Platelet-like nanoparticles: mimicking shape, flexibility, and surface biology of platelets to target vascular injuries. *ACS Nano*, (2014).
14. Olsson, M., Bruhns, P., Frazier, W. A., Ravetch, J. V. & Oldenborg, P. A. Platelet homeostasis is regulated by platelet expression of CD47 under normal conditions and in passive immune thrombocytopenia. *Blood* 105, 3577-3582, (2005).
15. Sims, P. J., Rollins, S. A. & Wiedmer, T. Regulatory control of complement on blood-platelets—modulation of platelet procoagulant responses by a membrane inhibitor of the C5b-9 Complex. *J. Biol. Chem.* 264, 19228-19235, (1989).
16. Nieswandt, B. & Watson, S. P. Platelet-collagen interaction: is GPVI the central receptor? *Blood* 102, 449-461, (2003).
17. Hu, C. M. et al. Erythrocyte membrane-camouflaged polymeric nanoparticles as a biomimetic delivery platform. *Proc. Natl. Acad. Sci. U.S.A.* 108, 10980-10985, (2011).
18. Hu, C. M., Fang, R. H., Copp, J., Luk, B. T. & Zhang, L. A biomimetic nanosponge that absorbs pore-forming toxins. *Nature Nanotech.* 8, 336-340, (2013).
19. Hu, C. M., Fang, R. H., Luk, B. T. & Zhang. L. Nanoparticle-detained toxins for safe and effective vaccination. *Nature Nanotech.* 8, 933-938, (2013).
20. Gachet, C. et al. Alpha IIb beta 3 integrin dissociation induced by EDTA results in morphological changes of the platelet surface-connected canalicular system with differential location of the two separate subunits. *J. Cell. Biol.* 120, 1021-1030, (1993).
21. Luk, B. et al. Interfacial interactions between natural RBC membranes and synthetic polymeric nanoparticles. *Nanoscale* 6, 2730-2737, (2013).
22. Jansen. A. J. et al. Desialylation accelerates platelet clearance after refrigeration and initiates GPIbalpha metalloproteinase-mediated cleavage in mice. *Blood* 119, 1263-1273, (2012).
23. Kalluri. R. Basement membranes: structure, assembly and role in tumour angiogenesis. Nature Rev. *Cancer* 3, 422-433, (2003).
24. Rodriguez, P. L. et al. Minimal "self" peptides that inhibit phagocytic clearance and enhance delivery of nanoparticles. *Science* 339, 971-975, (2013).
25. Law, S. K. A. & Dodds, A. W. The internal thioester and the covalent binding properties of the complement proteins C3 and C4. *Protein Sci.* 6, 263-274, (1997).
26. Terstappen, L. W. M. M., Nguyen, M., Lamarus, H. M. & Medof, M. E. Expression of the DAF (CD55) and CD59 antigens during normal hematopoietic-cell differentiation. *J. Leukocyte Biol.* 52, 652-660, (1992).

27. Andersen, A. J., Hashemi, S. H., Andresen, T. L., Hunter, A. C. & Moghimi, S. M. Complement: alive and kicking nanomedicines. J. Biomed. *Nanotech.* 5, 364-372, (2009).

28. Siboo, I. R., Chambers, H. F. & Sullam, P. M. Role of SraP, a serine-rich surface protein of *Staphylococcus aureus*, in binding to human platelets. *Infect. Immun.* 73, 2273-2280, (2005).

29. Kamaly, N. et al. Development and in vivo efficacy of targeted polymeric inflammation-resolving nanoparticles. *Proc. Natl. Acad. Sci. U.S.A.* 110, 6506-6511, (2013).

30. Hu, C. M. et al. 'Marker-of-self' functionalization of nanoscale particles through a top-down cellular membrane coating approach. *Nanoscale* 5, 2664-2668, (2013).

The invention claimed is:

1. A method for preventing and/or treating a tumor or a cancer associated with a damaged or leaky vasculature in a subject, which method comprises administering, to a subject in need, or to cells of said subject, an effective amount of a nanoparticle comprising a) an inner core comprising a non-cellular material, b) an outer surface comprising a cellular membrane derived from a platelet; and c) a single agent for preventing, treating, diagnosing, prognosing said tumor or a cancer and/or monitoring prevention or treatment of said tumor or a cancer, wherein said tumor or cancer is associated with tumor angiogenesis and said nanoparticle comprises an effective amount of a single angiogenesis inhibitor, wherein the angiogenesis inhibitor is angiostatin, endostatin, or tumstatin.

2. The method of claim 1, wherein the subject is a human.

3. The method of claim 1, wherein the inner core comprises a polymeric particle core.

4. The method of claim 1, wherein the inner core comprises a biocompatible or a synthetic material selected from the group consisting of poly(lactic-c-glycolic acid) (PLGA), polylactic acid (PLA), polyglycolic acid (PGA), polycaprolactone (PCL), polylysine, and polyglutamic acid.

5. The method of claim 1, wherein the inner core supports the outer surface.

6. The method of claim 1, wherein the cellular membrane comprises a plasma membrane derived from the platelet.

7. The method of claim 1, wherein the nanoparticle substantially lacks constituents of the platelet from which the cellular membrane is derived.

8. The method of claim 1, wherein the nanoparticle substantially maintains natural structural integrity or activity of the cellular membrane derived from the platelet or the constituents of the cellular membrane derived from the platelet.

9. The method of claim 1, wherein the nanoparticle substantially lacks immunogenicity to the subject.

10. The method of claim 9, wherein the cellular membrane is derived from a platelet from the same species of the subject.

11. The method of claim 1, wherein the tumor or cancer is selected from the group consisting of sarcoma, epidermoid cancer, fibrosarcoma, cervical cancer, gastric carcinoma, skin cancer, leukemia, lymphoma, lung cancer, non-small cell lung cancer, colon cancer, CNS cancer, melanoma, ovarian cancer, renal cancer, prostate cancer, breast cancer, liver cancer, head and neck cancers, and pancreatic cancer.

12. The method of claim 1, which further comprises administering another active ingredient to the subject.

13. The method of claim 1, which further comprises assessing efficacy of the nanoparticle and/or the another active ingredient in preventing and/or treating a tumor or a cancer associated with a damaged or leaky vasculature in a subject.

14. The method of claim 1, wherein the nanoparticle, alone or in combination with other active ingredient(s), is administered via oral, parenteral, rectal, nasal, topical, or ocular routes, or by inhalation.

15. The method of claim 14, wherein the parenteral administration is via intravenous, intramuscular, intraperitoneal, intranasal, or subcutaneous route.

16. The method of claim 1, wherein the method further comprises administering another agent for preventing, treating, diagnosing, prognosing the tumor or cancer and/or monitoring prevention or treatment of the tumor or a cancer in the subject.

17. The method of claim 1, wherein the angiogenesis inhibitor is endostatin, or tumstatin.

* * * * *